United States Patent
Mentzel et al.

(10) Patent No.: US 10,434,480 B2
(45) Date of Patent: Oct. 8, 2019

(54) WATER EXTRACTION SYSTEM CONTAINING A MEMBRANE INCLUDING AN ACTIVE LAYER HAVING A CROSS-LINKED AROMATIC POLYAMIDE THIN FILM

(71) Applicant: Aquaporin A/S, Copenhagen (DK)

(72) Inventors: Søren Junker Mentzel, København V (DK); Mark Edward Perry, The Cascadia (SG); Jörg Vogel, København S (DK); Sylvie Braekevelt, Frederiksberg (DK); Oliver Geschke, Kgs. Lyngby (DK); Marianne Eleonora Spanget Larsen, Store Heddinge (DK)

(73) Assignee: Aquaporin A/S, Kongens Lyngby (DK)

( * ) Notice: Subject to any disclaimer, the term of this patent is extended or adjusted under 35 U.S.C. 154(b) by 980 days.

(21) Appl. No.: 14/770,020

(22) PCT Filed: Feb. 24, 2014

(86) PCT No.: PCT/EP2014/053519
§ 371 (c)(1),
(2) Date: Aug. 24, 2015

(87) PCT Pub. No.: WO2014/128293
PCT Pub. Date: Aug. 28, 2014

(65) Prior Publication Data
US 2016/0016127 A1    Jan. 21, 2016

(30) Foreign Application Priority Data
Feb. 25, 2013 (DK) .................... 2013 00107

(51) Int. Cl.
*B01D 71/74*    (2006.01)
*B01D 65/02*    (2006.01)
(Continued)

(52) U.S. Cl.
CPC ............ *B01D 71/74* (2013.01); *A01C 23/042* (2013.01); *A61M 1/1623* (2014.02);
(Continued)

(58) Field of Classification Search
CPC ............... A01C 23/042; A61M 1/1623; B01D 2321/162; B01D 2321/168;
(Continued)

(56) References Cited

U.S. PATENT DOCUMENTS

| | | |
|---|---|---|
| 3,130,156 A | 4/1964 | Neff |
| 3,637,488 A | 1/1972 | Li et al. |

(Continued)

FOREIGN PATENT DOCUMENTS

| | | |
|---|---|---|
| EP | 1518564 A2 | 3/2005 |
| EP | 2113298 A1 | 11/2009 |

(Continued)

OTHER PUBLICATIONS

Achilli et al., "Selection of inorganic-based draw solutions for forward osmosis applications," J Membr Sci. 364:233-41 (2010).

(Continued)

*Primary Examiner* — Mark A Laurenzi
*Assistant Examiner* — Paul W Thiede
(74) *Attorney, Agent, or Firm* — Clark & Elbing LLP

(57) ABSTRACT

The present invention relates to a water extraction system comprising a flow cell comprising a membrane; said membrane comprising an active layer comprising immobilized aquaporin water channels and a support layer, and said membrane having a feed side and a non-feed side; and an aqueous source solution in fluid communication with the feed side of the membrane.

7 Claims, 8 Drawing Sheets

(51) Int. Cl.
| | | |
|---|---|---|
| B01D 67/00 | (2006.01) | |
| B01D 69/10 | (2006.01) | |
| B01D 71/56 | (2006.01) | |
| A01C 23/04 | (2006.01) | |
| B01D 61/00 | (2006.01) | |
| B01D 61/02 | (2006.01) | |
| B01D 61/08 | (2006.01) | |
| B01D 69/12 | (2006.01) | |
| B01D 69/14 | (2006.01) | |
| C02F 1/44 | (2006.01) | |
| A61M 1/16 | (2006.01) | |
| C02F 101/10 | (2006.01) | |
| C02F 101/16 | (2006.01) | |
| C02F 103/08 | (2006.01) | |

(52) U.S. Cl.
CPC .......... *B01D 61/002* (2013.01); *B01D 61/025* (2013.01); *B01D 61/08* (2013.01); *B01D 65/02* (2013.01); *B01D 67/0093* (2013.01); *B01D 69/10* (2013.01); *B01D 69/125* (2013.01); *B01D 69/144* (2013.01); *B01D 71/56* (2013.01); *C02F 1/441* (2013.01); *C02F 1/445* (2013.01); *B01D 2321/162* (2013.01); *B01D 2321/168* (2013.01); *B01D 2323/30* (2013.01); *C02F 2101/108* (2013.01); *C02F 2101/16* (2013.01); *C02F 2103/08* (2013.01); *Y02P 60/214* (2015.11); *Y02W 10/37* (2015.05)

(58) Field of Classification Search
CPC .............. B01D 2323/30; B01D 61/002; B01D 61/025; B01D 61/08; B01D 65/02; B01D 67/0093; B01D 69/10; B01D 69/125; B01D 69/144; B01D 71/56; B01D 71/74; B01D 61/14; C02F 1/1441; C02F 1/445; C02F 2101/108; C02F 2101/16; C02F 2103/08; Y02P 60/214; Y02W 10/37
USPC .................... 415/121.3; 210/643; 416/241 A
See application file for complete search history.

(56) References Cited

U.S. PATENT DOCUMENTS

| | | | |
|---|---|---|---|
| 3,740,421 A | 6/1973 | Schmolka et al. | |
| 3,897,308 A | 7/1975 | Li et al. | |
| 3,906,250 A | 9/1975 | Loeb | |
| 4,193,267 A | 3/1980 | Loeb | |
| 4,277,344 A | 7/1981 | Cadotte | |
| 4,360,448 A | 11/1982 | Li et al. | |
| 4,772,391 A | 9/1988 | Baker et al. | |
| 4,781,733 A | 11/1988 | Babcock et al. | |
| 4,966,708 A | 10/1990 | Oklejas et al. | |
| 5,229,004 A | 7/1993 | Skelland | |
| 5,262,054 A | 11/1993 | Wheeler | |
| 5,340,480 A | 8/1994 | Kawata et al. | |
| 5,741,416 A | 4/1998 | Tempest, Jr. | |
| 6,297,059 B1 | 10/2001 | Song et al. | |
| 7,014,531 B2 | 3/2006 | Hansen | |
| 7,208,089 B2 | 4/2007 | Montemagno et al. | |
| 7,424,485 B2 | 9/2008 | Kristiansen et al. | |
| 7,563,370 B2 | 7/2009 | Thorsen et al. | |
| 7,566,402 B2 | 7/2009 | Thorsen et al. | |
| 7,713,544 B2 | 5/2010 | Chaikof et al. | |
| 7,857,978 B2 | 12/2010 | Jensen et al. | |
| 8,123,948 B2 | 2/2012 | Jensen | |
| 9,278,316 B2 | 3/2016 | Vissing et al. | |
| 10,011,692 B2 | 7/2018 | Vogel et al. | |
| 10,293,094 B2 | 5/2019 | Larsen et al. | |
| 2001/0034432 A1 | 10/2001 | Sodroski et al. | |
| 2002/0107215 A1 | 8/2002 | Brown et al. | |
| 2003/0102263 A1 | 6/2003 | Lopez et al. | |
| 2004/0049230 A1 | 3/2004 | Montemagno et al. | |
| 2007/0087328 A1 | 4/2007 | Sleytr et al. | |
| 2007/0105094 A1 | 5/2007 | Fujita et al. | |
| 2007/0199892 A1 | 8/2007 | Peinemann et al. | |
| 2007/0275480 A1 | 11/2007 | Brander et al. | |
| 2008/0234462 A1 | 9/2008 | Yoo et al. | |
| 2009/0007555 A1* | 1/2009 | Jensen ................ B01D 69/141 60/326 |
| 2009/0074988 A1 | 3/2009 | Faris et al. | |
| 2009/0308727 A1 | 12/2009 | Kirts | |
| 2010/0006495 A1 | 1/2010 | Buschmann | |
| 2010/0178592 A1 | 7/2010 | Cinquin et al. | |
| 2010/0196203 A1 | 8/2010 | Sanghera et al. | |
| 2010/0270233 A1 | 10/2010 | Kim et al. | |
| 2010/0294714 A1 | 11/2010 | Buck et al. | |
| 2011/0020950 A1 | 1/2011 | Vogel et al. | |
| 2011/0046074 A1 | 2/2011 | Kumar et al. | |
| 2011/0084026 A1 | 4/2011 | Freger et al. | |
| 2011/0259815 A1 | 10/2011 | Montemagno | |
| 2011/0284456 A1 | 11/2011 | Brozell | |
| 2012/0080377 A1 | 4/2012 | Jensen et al. | |
| 2012/0152841 A1* | 6/2012 | Vissing ................. B01D 61/40 210/643 |
| 2012/0255862 A1 | 10/2012 | Dunnam et al. | |
| 2013/0240369 A1* | 9/2013 | McAlister ............... C25B 11/03 205/343 |
| 2013/0277307 A1 | 10/2013 | Jensen et al. | |
| 2014/0332468 A1 | 11/2014 | Tang et al. | |
| 2015/0144553 A1 | 5/2015 | Vogel et al. | |
| 2015/0273407 A1 | 10/2015 | Gil et al. | |
| 2015/0360183 A1 | 12/2015 | Jensen et al. | |
| 2016/0016127 A1 | 1/2016 | Mentzel et al. | |
| 2019/0076789 A1 | 3/2019 | Spulber et al. | |
| 2019/0184344 A1 | 6/2019 | Mentzel et al. | |

FOREIGN PATENT DOCUMENTS

| | | |
|---|---|---|
| EP | 2179780 A1 | 4/2010 |
| JP | 2005-083765 A | 3/2005 |
| JP | 2009-510301 A | 3/2009 |
| KR | 2010-0116344 A | 11/2010 |
| WO | WO-87/02380 A1 | 4/1987 |
| WO | WO-00/29337 A1 | 5/2000 |
| WO | WO-02/13955 A1 | 2/2002 |
| WO | WO-2004/011600 A2 | 2/2004 |
| WO | WO-2004-099088 A1 | 11/2004 |
| WO | WO-2007/033675 A1 | 3/2007 |
| WO | WO-2007/035987 A1 | 4/2007 |
| WO | WO-2009/074155 A1 | 6/2009 |
| WO | WO-2009/076174 A1 | 6/2009 |
| WO | WO-2009/155596 A2 | 12/2009 |
| WO | WO-2010/091078 A2 | 8/2010 |
| WO | WO-2013/039456 A1 | 3/2013 |
| WO | WO-2013/043118 A1 | 3/2013 |

OTHER PUBLICATIONS

Al-Amoudi et al., "Fouling strategies and the cleaning system of NF mebranes and factors affecting cleaning efficiency," J Membr Sci. 303:4-28 (2007).

Grosser, "The challenge: measure arsenic in drinking water," <http://www.watertechonline.com/articles/print/the-challeng-measure-arsenic-in-drinking-water>, retrieved on Feb. 22, 2013 (5 pages).

Hill et al., "Use of aquaporins to achieve needed water purity on the international space station for the extravehicular mobility unit space suit system," in Proceedings of the 42nd International Conference on Environmental Systems, San Diego, CA, USA (2012) (16 pages).

James-Smith et al., "Role of ethylene oxide and propylene oxide groups of pluronics in binding of fatty acid to pluronics in microemulsions," J Surfact Deterg. 11:237-42 (2008).

Kim et al., "Boron transport in forward osmosis: measurements, mechanisms, and comparison with reverse osmosis," J Membr Sci. 419-420:42-8 (2012).

Korikov et al., "Interfacially polymerized hydrophilic microporous thin film composite membranes on porous polypropylene hollow fibers and flat films," J Memb Sci. 279:588-600 (2006).

(56) References Cited

OTHER PUBLICATIONS

Nagaishi et al., "A simple method for the precise determination of boron, zirconium, niobium, hafnium and tantalum using ICP-MS and new results for rock references samples," Geochemical Journal. 43:133-41 (2009).
Petrusevski et al., "Arsenic in drinking water," IRC International Water and Sanitation Centre. 17:1-57 (2007).
Phuntsho et al., "A novel low energy fertilizer driven forward osmosis desalination for direct fertigation: evaluating the performance of fertilizer draw solutions," J Membr Sci. 375:172-81 (2011).
Porcelli et al., "Chemical cleaning of potable water membranes: a review," Sep Purif Technol. 71:137-43 (2010).
Sam et al., "Composition and clinical use of hemodialysates," Hemodial Int. 10(1):15-28 (2006).
Search Report for Danish Application No. PA 201300107, dated Jun. 20, 2013 (1 page).
Wang et al. "Characterization of novel forward osmosis hollow fiber membranes" Journal of Membrane Science. 355:158-67 (2010).
Öberg et al., "Glycosylation increases the theromostability of human aquaporin 10 protein," J Biol Chem. 286(36):31915-23 (2011) (19 pages).
"Ultrapes™ Membrane and P.E.T.® Technology" <http://www.membrana.com/index.php/21-uncategorised/146-liqui-fluxr-water-modules-product-information39>, retrieved on Jan. 27, 2015 (2 pages).
Agre et al., "The aquaporins, blueprints for cellular plumbing systems," J Biol Chem. 273(24):14659-62 (1998).
Aoike, "Required Water Quality for the Use of High-Performance Membranes," Contrib Nephrol. 173: 53-57 (2011).
Becker et al., "Membrane Proteins: The 'Mosaic' Part of the Model," The World of the Cell. Ruggirello, 171-174,203 (2006).
Borgnia et al., "Cellular and molecular biology of the aquaporin water channels," Annu Rev Biochem. 68:425-58 (1999).
Brian et al., "Allogeneic stimulation of cytotoxic T cells by supported planar membranes," Proc Natl Acad Sci U.S.A. 81(19):6159-63 (1984).
Burykin et al., "What really prevents proton transport through aquaporin? Charge self-energy versus proton wire proposals," Biophys J. 85(6):3696-706 (2003).
Cath et al., "Forward osmosis: principles, applications, and recent developments," J Memb Sci. 281(1):70-87 (2006).
Chakrabarti et al., "Molecular basis of proton blockage in aquaporins," Structure 12(1):65-74 (2004).
Clark et al., Properties of Membranes Used for Hemodialysis Therapy. Seminars in Dialysis. Clark, 191-195 (2002).
Coury et al., "Reconstitution of water channel function of aquaporins 1 and 2 by expression in yeast secretory vesicles", Am J Physiol Renal Physiol. 274:34-42 (1998).
Cremer et al., "Formation and spreading of lipid bilayers on planar glass supports," J Phys Chem B. 103:2554-9 (1999).
Dainty et al., "Unstirred layers in frog skin," J Physiol. 182(1):66-78 (1966).
De Groot et al., "The mechanism of proton exclusion in the aquaporin-1 water channel," J Mol Biol. 333(2):279-93 (2003).
De Groot et al., "Water permeation across biological membranes: mechanism and dynamics of aquaporin-1 and GlpF," Science 294(5550):2353-7 (2001).
Deamer et al., "Large volume liposomes by an ether vaporization method," Biochim Biophys Acta. 443(3): 629-34 (1976).
Döring et al., "Enhanced internal dynamics of a membrane transport protein during substrate translocation," Protein Sci. 9(11):2246-50 (2000).
Fettiplace et al., "Water permeability of lipid membranes," Physiol Rev. 60(2):510-50 (1980).
Fissell et al "Development of continuous implantable renal replacement: past and future", Trans Res. 150(6):327-336 (2007).
Fu et al., "Structure of a glycerol-conducting channel and the basis for its selectivity," Science. 290(5491):481-6 (2000).

Gonen et al., "The structure of aquaporins," Q Rev Biophys. 39(4):361-96 (2006).
Hansen et al., "Formation of giant protein vesicles by a lipid cosolvent method," Chembiochem. 12(18):2856-62 (2011).
Hansen et al., "Large scale biomimetic membrane arrays," Anal Bioanal Chem. 395(3):719-27 (2009).
Heymann et al., "Aquaporins: Phylogeny, Structure, and Physiology of Water Channels," News Physiol Sci. 14:187-193 (1999).
Heyse et al.,"Emerging techniques for investigating molecular interactions at lipid membranes," Biochim Biophys Acta. 1376(3):319-38 (1998).
Hunter et al., "Effect of extrusion pressure and lipid properties on the size and polydisperity of lipid vesicles," Biophys J. 74(6):2996-3002 (1998).
Ilan et al., "The mechanism of proton exclusion in aquaporin channels," Proteins. 55(2):223-8 (2004).
International Search Report and Written Opinion for International Application No. PCT/EP2014/053519, dated Jul. 30, 2014 (24 pages).
Jensen et al., "Electrostatic tuning of permeation and selectivity in aquaporin water channels," Biophys J. 85(5):2884-99 (2003).
Judge et al., "Potassium channel blockers in multiple sclerosis: neuronal Kv channels and effects of symptomatic treatment," Pharmacol Ther. 111(1):224-59 (2006).
Karlsson et al., "Reconstitution of water channel function of an aquaporin overexpressed and purified from pichia pastoris," FEBS Lett. 537(1-3):68-72 (2003).
Koehorst et al., "Site-directed fluorescence labeling of a membrane protein with BADAN: probing protein topology and local environment," Biophys J. 94(10):3945-55 (2008).
Kotelyanskii et al., "Atomistic simulation of water and salt transport in the reverse osmosis membrane FT-30," J Memb Sci. 139: 1-16 (1998).
Laboratory of Membrane Processes Slovakia, "Available Equipment," <http://sschi.chtf.stuba.sk/MembraneLab/Equipment.htm>, retrieved on Dec. 15, 2011 (6 pages).
Lapointe et al., "Kinetics of carrier-mediated ion transport in two new types of solvent-free lipid bilayers," Biophys J. 39(2):141-50 (1982).
Lau et al., "A recent progress in thin film composite membrane: a review," Desalination. 287:190-9 (2012).
Leonenko et al., "Supported planar bilayer formation by vesicle fusion: the interaction of phospholipid vesicles with surfaces and the effect of gramicidin on bilayer properties using atomic force microscopy," Biochim Biophys Acta. 1509(1-2):131-47(2000).
Lin et al., "Amyloid beta protein forms ion channels: implications for Alzheimer's disease pathophysiology," FASEB J. 15(13):2433-44 (2001).
Low, "Preliminary studies of seawater desalination using forward osmosis," Desalination and Water Treatment. 7:41-6 (2009).
Maurer et al., "Spontaneous entrapment of polynucleotides upon electrostatic interaction with ethanol-destabilized cationic liposomes," Biophys J. 80(5):2310-26 (2001).
Mayer et al., "Vesicles of variable sizes produced by a rapid extrusion procedure," Biochim Biophys Acta. 858(1):161-8 (1986).
McGinnis et al., "Energy requirements of ammonia-carbon dioxide forward osmosis desalination," Desalination. 207:370-82 (2007).
Merzlyakov et al., "Directed assembly of surface-supported bilayers with transmembrane helices," Langmuir. 22(3):1247-53 (2006).
Montal et al., "Formation of biomolecular membranes from lipid monolayers and a study of their electrical properties," Proc Natl Acad Sci U.S.A. 69(12):3561-6 (1972).
Mou et al., "Gramicidin A aggregation in supported gel state phosphatidylcholine bilayers," Biochemistry. 35(10):3222-6 (1996).
Mui et al., "Osmotic properties of large unilamellar vesicles prepared by extrusion," Biophys J. 64(2):443-53 (1993).
Murata et al., "Structural determinants of water permeation through aquaporin-1," Nature. 407(6804):599-605 (2000).
Niwa et al., "The protein metabolite hypothesis, a model for the progression of renal failure: an oral adsorbent lowers indoxyl sulfate levels in undialyzed uremic patients," Kidney Int Suppl. 62:S23-S28 (1997).

(56) References Cited

OTHER PUBLICATIONS

Niwa, "Uremic toxicity of indoxyl sulfate," Nagoya J Med Sci. 72(1-2):1-11 (2010).
Norris et al., "High flux polyamide composite hollow fiber membranes for reverse osmosis applications," MRS Proceedings (MRS Spring Meeting). 930: Abstract (2006) (1 page).
Pohl et al., "Highly selective water channel activity measured by voltage clamp: analysis of planar lipid bilayers reconstituted with purified AqpZ," Proc Natl Acad Sci U.S.A. 98(17):9624-9 (2001).
Pohl et al., "The effect of a transmembrane osmotic flux on the ion concentration distribution in the immediate membrane vicinity measured by microelectrodes," Biophys J. 72(4):1711-8 (1997).
Preston et al., "Appearance of water channels in Xenopus oocytes expressing red cell CHIP28 protein," Science. 256(5055):385-7 (1992).
Reimhult et al., "Intact vesicle adsorption and supported biomembrane formation from vesicles in solution: influence of surface chemistry, vesicle size, temperature, and osmotic pressure," Langmuir. 19:1681-91 (2003).
Ren et al., "Visualization of water-selective pore by electron crystallography in vitreous ice," Proc Natl Acad Sci U.S.A. 98(4):1398-403 (2001).
Reviakine et al., "Formation of supported phospholipid bilayers from unilamellar vesicles investigated by atomic force microscopy," Langmuir. 16:1806-15 (2000).
Rinia et al., "Visualization of highly ordered striated domains induced by transmembrane peptides in supported phosphatidylcholine bilayers," Biochemistry. 39(19):5852-8 (2000).
Salafsky et al., "Architecture and function of membrane proteins in planar supported bilayers: a study with photosynthetic reaction centers," Biochemistry. 35(47):14773-81 (1996).
Saparov et al., "Water and ion permeation of aquaporin-1 in planar lipid bilayers. Major differences in structural determinants and stoichiometry," J Biol Chem. 276(34):31515-20 (2001).
Schiermeier, "Water: purification with a pinch of salt," Nature. 452(7185):260-1 (2008).
Shi et al., "Effect of substrate structure on the performance of thin-film composite forward osmosis hollow fiber membranes," J Memb Sci. 382:116-23 (2011).
Simon et al., "The noneffect of a large linear hydrocarbon, squalene, on the phosphatidylcholine packing structure," Biophys J. 19(1):83-90 (1977).
Simonsen et al., "Structure of spin-coated lipid films and domain formation in supported membranes formed by hydration," Langmuir. 20(22):9720-8 (2004).
Su et al., "Polyethersulfone Hollow Fiber Membranes for Hemodialysis," <http://www.intechopen.com/books/progress-in-hemodialysis-from-emergent-biotechnology-to-clinical-practice/polyethersulfone-hollow-fiber-membranes-for-hemodialysis >, retrieved on Mar. 9, 2015 (29 pages).
Sui et al., "Structural basis of water-specific transport through the AQP1 water channel," Nature. 414(6866):872-8 (2001).
Sukitpaneenit et al., "High performance thin-film composite forward osmosis hollow fiber membranes with macrovoid-free and highly porous structure for sustainable water production," Environ Sci Technol. 46(13): 7358-7365 (2012).
Szoka et al., "Comparative properties and methods of preparation of lipid vesicles (liposomes)," Annu Rev Biophys Bioeng. 9:467-508 (1980).
Tajkhorshid et al., "Control of the selectivity of the aquaporin water channel family by global orientation tuning," Science. 296(5567):525-30 (2002).
Tang et al., "Desalination by biomimetic aquaporin membranes: Review of status and prospects," Desalination. 308:34-40 (2013).
Keller, Danielle, Thesis, "Chapter 4: Reconstitution of Cytochrome C Oxidase," University of Southern Denmark, 2005.
Planar Lipid Bilayers (BLMs) and their Applications, Membrane Science and Technology Series 7. Tien and Ottova-Leitmannova, 381-382, 450-454, 807-819, 825-829 (2003).
Tokumasu et al., "Nanoscopic lipid domain dynamics revealed by atomic force microscopy," Biophys J. 84(4):2609-18 (2003).
Van Kan et al., "The peptide antibiotic clavanin A interacts strongly and specifically with lipid bilayers," Biochemistry 42(38):11366-72 (2003).
Verissimo et al., "Thin-film composite hollow fiber membranes: An optimized manufacturing method," J Memb Sci. 246:48-55 (2005).
Waldbillig et al., "Planar bilayer membranes from pure lipids," Biochim Biophys Acta 557(2):295-305 (1979).
Wang et al., "FI/SI on-line solvent extraction/back extraction preconcentration coupled to direct injection nebulization inductively coupled plasma mass spectrometry for determination of copper and lead," J Anal At Spectrom. 17(10):1284-9 (2002).
Wang et al., "What makes an aquaporin a glycerol channel? A comparative study of AqpZ and GlpF," Structure. 13(8):1107-1118 (2005).
Webber et al., "Hydrodynamic studies of adsorbed diblock copolymers in porous membranes," Macromolecules. 23:1026-34 (1990).
White, "Formation of "solvent-free" black lipid bilayer membranes from glyceryl monooleate dispersed in squalene," Biophys J. 23(3):337-47 (1978).
Xie, "Alteration of Membrane Properties during Continuous Hemofiltration Therapy in vivo," <http://darwin.bth.rwth-aachen.de/opus3/volltexte/2011/3556/pdf/3556.pdf>, retrieved on Mar. 11, 2015 (102 pages).
Yang et al., "Dual-Layer Hollow Fibers with Enhanced Flux as Novel Forward Osmosis Membranes for Water Production," Environ. Sci. Technol. 43(8):2800-2805 (2009).
Zeidel et al., "Reconstitution of functional water channels in liposomes containing purified red cell CHIP28 protein," Biochemistry. 31(33):7436-40 (1992).
Zhao et al "Synthesis of robust and high-performance aquaporin-based biomimetic membranes by interfacial polymerization-membrane preparation and RO performance characterization", J Memb Sci. 423-424:422-428 (2012).
Zhong et al., "Development of Thin-Film Composite forward Osmosis Hollow Fiber Membranes Using Direct Sulfonated Polyphenylenesulfone (sPPSU) as Membrane Substrates," Environ. Sci. Technol. 47(13):7430-7436 (2013).
Zhu et al., "Theory and simulation of water permeation in aquaporin-1," Biophys J. 86(1 PT 1):50-7 (2004).

* cited by examiner

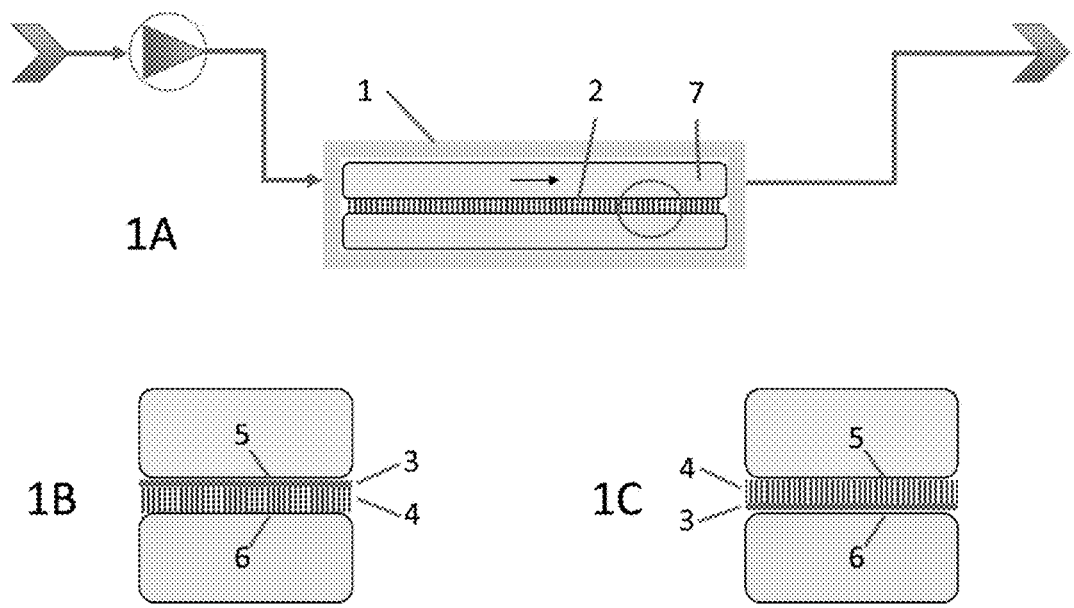
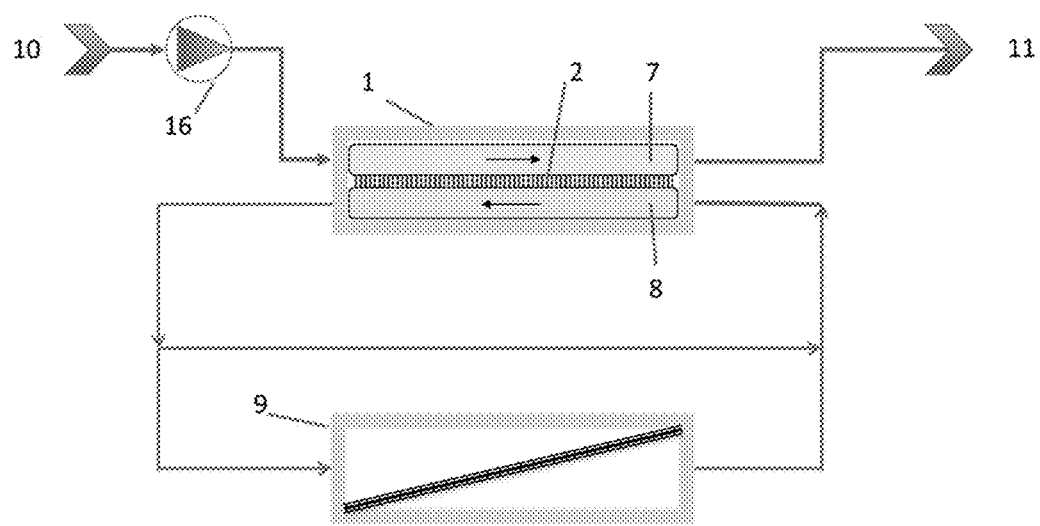
Fig. 1
Fig. 2

WATER EXTRACTION SYSTEM CONTAINING A MEMBRANE INCLUDING AN ACTIVE LAYER HAVING A CROSS-LINKED AROMATIC POLYAMIDE THIN FILM

FIELD OF THE INVENTION

The present invention relates to a system for water extraction said system comprising a flow cell housing a filter membrane, where said membrane has an active layer comprising immobilized aquaporin water channels, and a porous support layer, and where an aqueous source solution is in fluid communication with said membrane. In addition, the invention relates to systems for removal of contaminants from water sources, systems for generation of diluted nutrient solutions for irrigation purposes using fertilizer drawn forward osmosis, systems for concentrating organic and/or inorganic solutes in aqueous solutions, water extraction systems using forward osmosis and/or reverse osmosis in general, such as low pressure reverse osmosis, systems for pressure retarded osmosis, waste water or process water treatment including extraction of water from used dialysate solutions, and combined systems for desalination and/or energy generation having low or zero carbon emission.

BACKGROUND OF THE INVENTION

Water is the most essential component of life. However, with the growing scarcity of clean water, more and more interest is being paid to extraction of clean water from seawater and industrial water and to treatment of industrial process water and difficult wastewater streams. There is also an interest in the possibility of gentle water extraction from valuable solutions—from food streams to solutions of proteins and peptides or valuable small organic compounds.

Among different water purification techniques, reverse osmosis, forward osmosis and nanofiltration have become popular for water extraction because of their effectiveness in removing low molecular weight solutes, such as small organic compounds and ions. However, these water extraction techniques are still energy-intensive and not always sufficiently selective. Examples are contaminants, such as dissolved boron compounds naturally present in seawater and in contaminated groundwater, and which can pose a problem in desalinated water for irrigation and drinking water, and arsenic compounds that are frequently present in natural surface and ground water sources, e.g. in alluvial plains and moraine deposits.

Kim et al. 2012 studied boron rejection in various FO and RO water filtration experiments and found a maximum boron retention of about 50 to 55% in FO mode. However, this low boron filtration efficiency may necessitate several filtration cycles in order to obtain a desired low boron content in the resulting filtrate. Thus it is crucial to develop improved water extraction systems, such as systems that are able to remove water contaminants, such as boron or arsenic, and preferably in few or only one filtration step(s). In addition, it is a purpose of the invention to provide a water extraction system adapted for fertilizer drawn forward osmosis (FDFO), where seawater, brackish water, impaired ground or surface water or any other suitable water source can be used as a feed solution and a concentrated inorganic plant nutrient solution is used as a draw solution resulting in a final fertilizer solution having a sufficiently low osmolality or boron content as to allow it to be used as a liquid fertilizer, e.g. as irrigation water with added nutrients. Moreover, it is a purpose of the invention to provide a novel system for energy storage as well as a novel system for reuse of water, such as ultrapure water, in hemodialysis.

SUMMARY OF THE INVENTION

It is an object of the present invention to provide a water extraction system utilizing aquaporin water channels immobilized in or on a supported filter membrane, such as in the form of a supported or immobilized liquid membrane formulation. With reference to FIG. 1 said system comprises a flow cell (1) comprising a membrane (2) where said membrane comprises an active layer (3) comprising aquaporin water channels and a porous support layer (4), and said membrane having a feed side (5) and a non-feed side (6); and said system further comprising an aqueous source solution (7) in fluid communication with said feed side. The present invention provides a novel system for selective water extraction, wherein a filter membrane incorporating aquaporin water channels, such as the aquaporin Z water channels, provide to the system the unique and selective water transporting properties of said channels, i.e. highly efficient water flux, high salt rejection, low energy consumption in forward osmosis operation mode, high rejection of small organic and inorganic solutes, intrinsic low fouling propensity, and robust operation conditions, especially of the membranes used in the system.

Other objects of the invention will be apparent to the person skilled in the art from the following detailed description and examples.

BRIEF DESCRIPTION OF THE DRAWINGS

FIG. 1A shows a schematic diagram of the essential features of a water extraction system, wherein: (1) is the flow cell; (2) is the membrane; and (7) is the aqueous source solution. FIG. 1B shows the embodiment where the active layer (3) is on the feed side (5) of the membrane and the support layer (4) is on the non-feed side (6) of the membrane. The FIG. 1B membrane configuration has shown higher rejection % of boron containing solutes in some experiments, cf. Example 1. FIG. 1C shows the embodiment where the support layer (4) is on the feed side (5) of the membrane and the active layer (3) is on the non-feed side (6) of the membrane.

FIG. 2 shows a schematic diagram of a Forward Osmosis (FO) system for water extraction from a feed stream, wherein: (10) is the feed stream; (1) is the flow cell with the membrane (2); (11) is the concentrated feed stream; (8) is the draw solution in fluid communication with the draw side of the membrane; and (9) is a draw solution concentration unit (9).

DETAILED DESCRIPTION OF THE INVENTION

Figure 3:
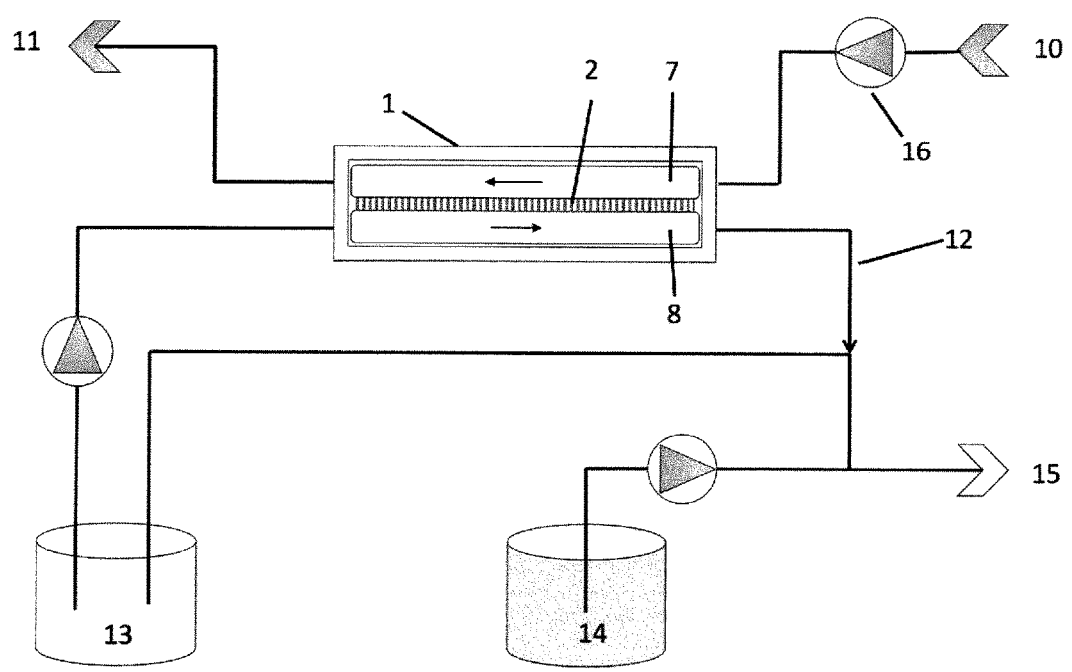
FIG. 3 shows a schematic diagram of a Fertilizer Drawn Forward Osmosis (FDFO) desalination system, wherein: (10) is the feed stream, preferably of non-potable water; (13) is the concentrated fertilizer solution; (1) is the flow cell with the membrane; (12) is the partly diluted fertilizer solution which can be re-circulated to achieve higher degree of dilution; (14) is the additional freshwater tank for final adjustment of the degree of dilution of the fertilizer solution; (11) is the concentrated feed stream, e.g. up-concentrated seawater; (15) is the diluted fertilizer solution ready for use.

More specifically, the invention relates to systems for water extraction as detailed below.

Water Extraction System with Removal of Contaminants

The present invention relates to systems using RO and or FO for the removal of contaminants, such as trace contaminants including heavy metals and toxic inorganic compounds, from water sources. Examples include removal of boron contamination from fresh water sources to be used for various purposes where boron is unwanted, e.g. for human consumption. Boron is an especially troublesome contamination in sea water sources when these are used for desalination to produce irrigation water and potable water. Existing technologies require two filtration passes in order to obtain sufficiently low boron concentration. The system of the invention offers removal of up to about 65% of the dissolved boron in a fresh water source at about neutral pH after only one RO pass and up to about 75% removal during an FO process at neutral pH, cf. the Example 1 below. Another example is the removal of arsenic contamination where the system of the invention can remove about 100% after both RO and FO filtration, cf. Example 2 below.

Water Extraction System for Fertilizer Drawn Forward Osmosis Desalination (FDFO)

Recently, there has been increasing interest in substituting diminishing freshwater sources with desalinated water for irrigation of crops, and further addition of diluted nutrient salt solutions to the irrigation water (FDFO). However, there are disadvantages in connection with the use of available FO membranes, such as the membranes that may be obtained from the Hydro well filter modules (Hydration Technologies Inc.) the disadvantage being mainly the relatively large reverse salt flux (Js) of the nutrient salts, e.g. potassium chloride, where figures as high as 59.58 $g/m^2h$ have been mentioned in the literature (0.222 $mmoles/m^2s$, Phuntsho et al. 2011) or 6.8 to 15.3 $g/m^2$ h (Achilli et al. 2010 using a flat-sheet cellulose triacetate (CTA) membrane from Hydration Technology Innovations, LLC, Scottsdale, Ariz.). It is desirable to have as low as possible a Js in order to minimize loss of the valuable nutrient ions. Herein we show that it is possible to obtain Js of less than 4 $g/m^2$ h in an FO system using a TFC-AqpZ membranes with amphiphile P8061 as vesicle forming substance (prepared according to the experimental section below), a 2 M KCl solution as draw, and deionized water with 5 µM calcein as feed, cf. the table below:

| Draw, FO chamber | $J_w$ [$L/m^2h$] | $J_{s,total}$ [$g/m^2h$] | $R_{calcein}$ [%] | Run time Min |
|---|---|---|---|---|
| 2M KCl, CF042 | 10.3 | 3.08 | 99.94 | 900 |
| 2M KCl, CF042 | 11.47 | 3.32 | 99.95 | 900 |
| 2M KCl, CF042 | 10.87 | 3.91 | 99.95 | 900 |
| 2M KCl, CF042 | 12.56 | 3.69 | 99.97 | 900 |
| 2M KCl, CF042 | 11.87 | 3.03 | 99.78 | 900 |
| 2M KCl, CF042 | 10.32 | 3.49 | 99.96 | 900 |
| 2M KCl, CF042 | 10.86 | 3.36 | 99.94 | 900 |

The table clearly shows that a consistent low reverse salt flux of average 3.41 [$g/m^2h$] can be obtained for the potassium salt KCl.

In addition, the present invention provides a low-energy means of reducing freshwater consumption in agriculture by as much as about 40% through the utilization of lower-grade or non-potable water supplies such as polluted groundwater, brackish water and even seawater. The water extraction system of the invention with its unique aquaporin membrane, such as in the form of a TFC membrane as prepared according to the experimental section herein, is used in combination with a liquid concentrated fertilizer draw solution to selectively extract clean water from the lower-grade water supplies herein utilized as feed source. The end result is a diluted liquid plant nutrient solution, which requires less freshwater to be ready for use for agricultural irrigation and fertilization. In the example below we describe how membrane tests have shown proof-of-concept in the case where the lower-grade water supply is relatively low-salinity of about 10 to 15 o/oo seawater from Øresund in Denmark.

A Water Extraction System with Separation of Urea from Urine in Space

We have together with scientists from the NASA Ames facilities in Palo Alto (CA, US) performed first real field tests with the system comprising an aquaporin membrane. Tests concluded that the water extraction system comprising the specific TFC-aquaporin membranes show superior rejection values to urea (>90%) when compared to existing forward osmosis membranes, cf. Hill & Taylor (2012). The water extraction system of the invention will contribute to the major effort of reducing the mass needed to transport into space on manned space missions, i.a. by re-circulating bodily fluids from the astronauts. It was concluded that a water extraction system according to the invention comes very close to fulfilling the requirements for a simple, lightweight and reliable system to extract potable water from body fluids in space.

In May 2012, scientists from Aquaporin A/S and NASA Ames successfully repeated testing at the NASA Ames facilities with up-scaled TFC-aquaporin membrane samples (500 cm$^2$). The up-scaled membrane samples performed identically to the initial samples thus proving the stability of the membrane production protocols. Based on the successful second tests, Aquaporin A/S and NASA Ames are investigating how to produce the first prototype system for yellow water re-use in space.

A Water Extraction System with Separation of Urea from RO Permeate in Dairy Industries Background: Many industrial effluents contain high concentrations of compounds including non-polar solutes such as urea, which are not removed by de-ionized water processes or reverse osmosis membranes. Said non-polar solutes are often chemically stable, and therefore not easily destroyed by UV sterilization processes. The state of the art treatment of urea wastewaters generally involves two steps: first, the hydrolysis of urea into ammonia and carbon dioxide and, second, the elimination of ammonia. Current methods mostly rely on anaerobic conditions for the biological treatment of high-strength urea wastewaters. However the required nitrifying bacteria have slow growth rates, a small acceptable pH-range, and are often inhibited by other wastewater contaminants (e.g. dicyandiamide). An advantage of the present system is that it is based on the use of a flow cell equipped with a membrane having immobilized aquaporin water channels, said membranes have shown very high urea removal in lab scale, cf. Example 7 below. This will eliminate the need for bioreactor technology and in principle allow for simple retrofitting of existing unit operations (e.g. polishing steps) currently employed in urea removal.

The high rejection and water flux properties of the aquaporin membrane and the intrinsic low fouling propensity makes it feasible and valuable to employ these biomimetic membranes into large scale industrial systems for urea removal, where there is a potential for fouling and/or a need to up-concentrate small neutral solutes (e.g. urea)—not readily achievable with current technology—membrane based or other. The high rejection towards urea enables the system of the invention to be used for treatment of wastewater streams containing high amounts of urea, such as is present in process water from dairies. In one embodiment of the water extraction system of the invention, the aquaporin membrane, such as a TFC-membrane comprising immobilized aquaporin water channels, will be used together with a high osmolarity draw solution (e.g. seawater e.g. from Kattegat) to extract close to urea-free water from the wastewater streams. This low-energy water extraction system will effectively reduce disposal costs through wastewater volume reduction.

Figure 6:
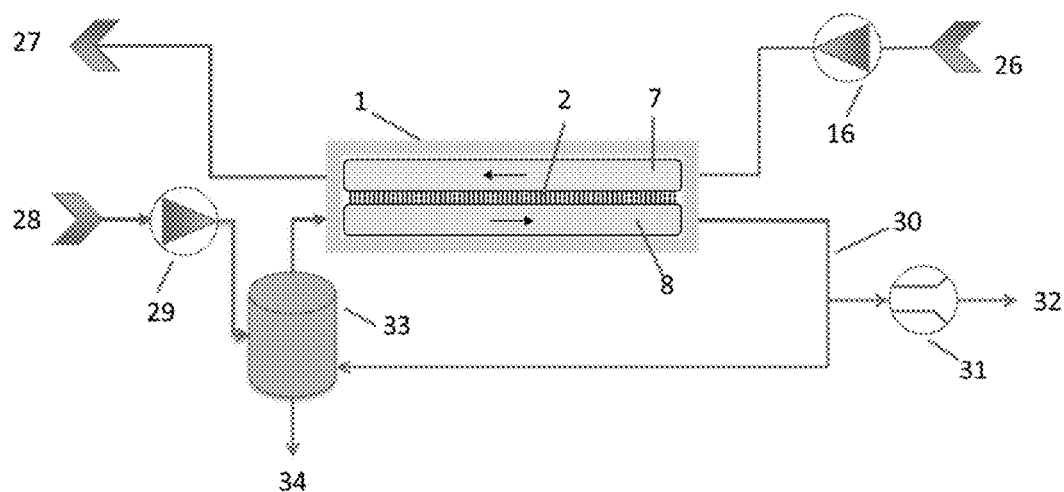
FIG. 6 shows a schematic diagram of a pressure retarded osmosis (PRO) system, wherein: (1) is the flow cell with the membrane (2); (26) is the feed stream, e.g. fresh water or seawater having a lower osmolality than the draw stream; (16) is a pump; (27) is the feed water bleed; (28) is the draw stream, e.g. seawater or brine; (29) is a pump; (30) is the diluted and pressurized draw stream; (31) is a turbine to generate power; (32) and (34) are depressurized draw water; and (33) is a pressure exchanger to assist in pressurizing the incoming draw stream.

Water Extraction System for Up-Concentration of Solutes in a Wide Range of Aqueous Solutions by Forward Osmosis, Cf. FIG. 6

Figure 8:
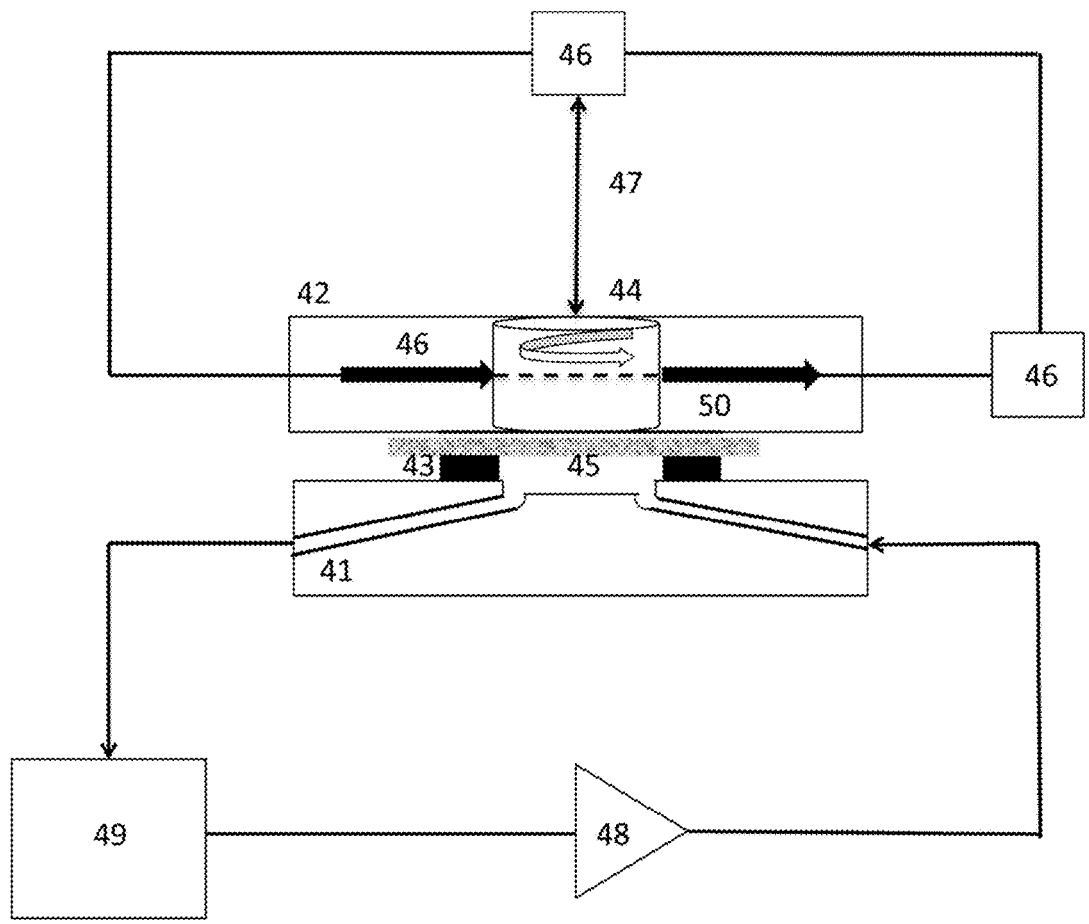
FIG. 8 shows a schematic diagram of a modified FO concentrator, wherein (41) is the base unit containing a customized flow inlet and flow outlet to ensure an optimal draw solution flow profile beneath the membrane (45), the base unit contains a securing mechanism for the disposable top unit (42); (43) is an O-ring to secure and seal the flow cell; (44) is an optional flow generator to stir the solution in the top unit; (46) is an inline monitoring system to monitor and continuously display the degree of concentration in the top unit feed solution; (47) is the feedback loop mechanism designed to stop the concentration process once the desired concentration is reached; (48) is a pump to recirculate the draw solution; and (49) is a disposable draw solution pouch containing customized draw solution for different concentration processes; and (50) is an optional mesh support above the membrane (45) to provide stability.
Figure 9:
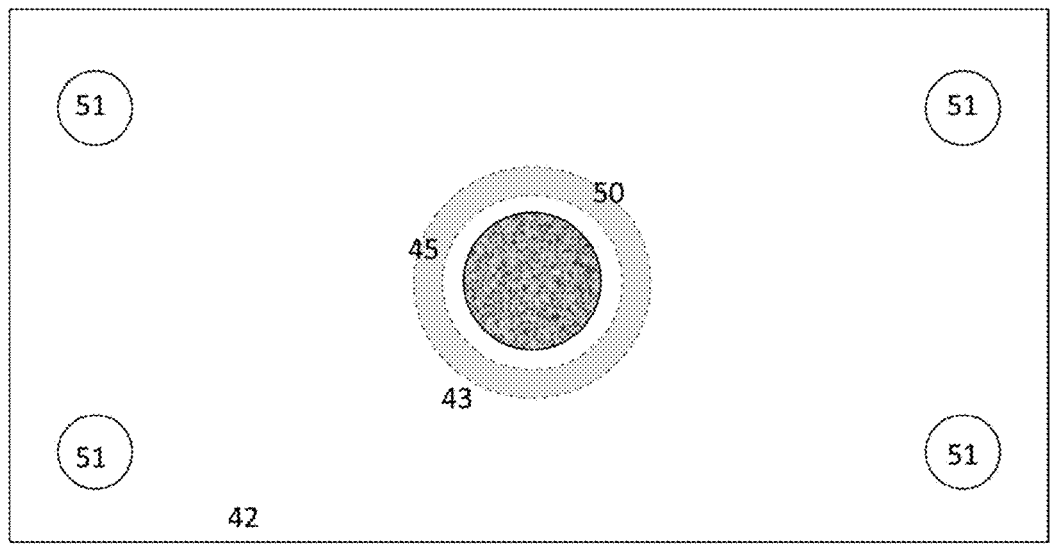
FIG. 9 shows a schematic diagram of the top unit of the FO concentrator in FIG. 8 seen from above, wherein (51) are means for the clamping together of the top and the base units.
Figure 10:
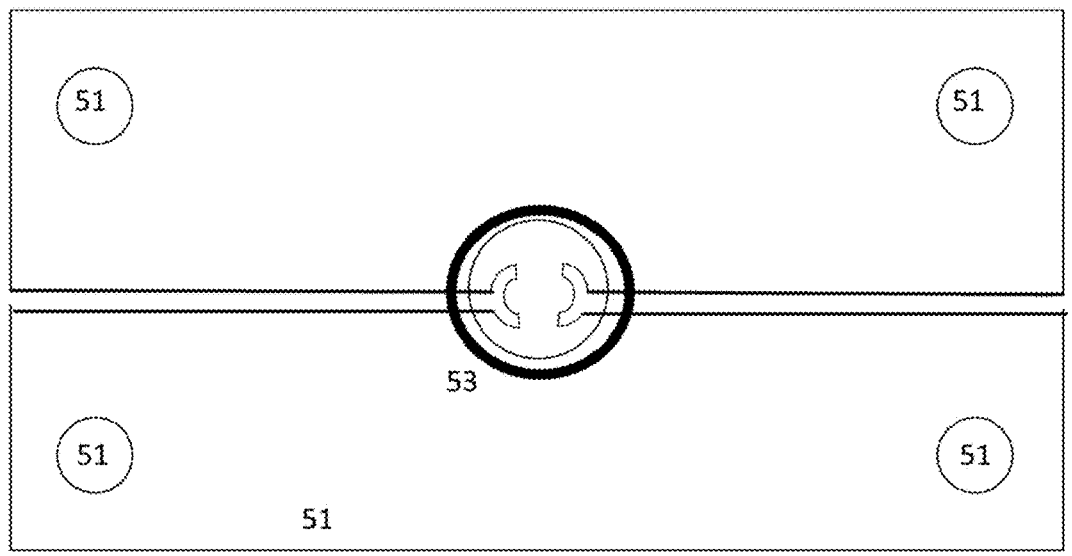
FIG. 10 shows a schematic diagram of the base unit of the FO concentrator in FIG. 8 seen from above.

In this system a high osmolarity or osmolality draw solution, such as brine, is used in combination with an aquaporin membrane, such as the TFC membrane prepared as described herein, to up-concentrate aqueous solutions in a forward osmosis process. Aqueous solutions of interest include difficult wastewater streams, pharmaceutical and biological product solutions and liquid foodstuffs. An exemplary embodiment is a system for up-concentration of organic molecules of a wide range of molecular sizes, such as amino acids and oligopeptides to proteins including membrane proteins which are normally concentrated to a desirable degree by centrifugal concentrators, e.g. using Pierce Concentrators that are available for 3K, 10K, 30K, and 100K molecular-weight cutoff (MWCO), and which concentrate and desalt biological samples with polyether sulfone (PES)-membrane ultrafiltration centrifugal devices. Advantages of the system according to the invention include a very gentle extraction of water, low peptide or protein loss, ability to concentrate a wide range of molecular sizes from amino acids to small peptides to large membrane proteins, a concentration process that is controllable and can be automated for high throughput in contrast to centrifugal concentrators presently on the market, or alternatively, concentrating the sample solution by vacuum drying, which is, however, often followed by severe loss of sample material and in additional contaminations. The system of the invention may be set up with a concentrator cell with either fixed aquaporin membrane for single use or with a removable aquaporin membrane as shown in FIG. 8. Thus, where the aquaporin membrane can be removed, e.g. for cleaning, and refitted into the cell, it is suggested that an EDTA or citric acid treatment as described in examples 4 and 5 below could be applied to the membrane while preserving the water extracting properties of the system.

Definitions

"Feed solution" means a solution of solutes in water.

"Draw solution" means a solution of higher osmotic pressure, relative to that of the feed solution. The draw solution may comprise a draw solute selected from at least one of water-soluble inorganic chemicals and water-soluble organic chemicals. The water-soluble inorganic chemicals may include at least one of $Al_2(SO_4)_3$, $MgSO_4$, $Na_2SO$, $K_2SO_4$, $(NH_4)_2SO_4$, $Fe_2(SO_4)_3$, $AlCl_3$, $MgCl_2$, NaCl, $CaCl_2$, $NH_4Cl$, KCl, $FeCl_3$, $Al(NO_3)_3$, $Mg(NO_3)_2$, $Ca(NO_3)_2$, $NaNO_3$, $NO_3$, $NH_4HCO_3$, $KHCO_3$, $NaHCO_3$, KBr and their relative hydrates; and wherein the water-soluble organic chemicals include at least one of methanol, ethanol, acetone, glucose, sucrose, fructose, dextrose, chitosan, dendrimer and 2-methylimidazole-based chemicals.

"Forward osmosis" (FO) is an osmotic process in which an osmotic pressure gradient across a semi-permeable membrane results in extraction of water from dissolved solutes. The driving force for inducing a net flow of water through the membrane is an osmotic pressure gradient from a draw solution of higher osmotic pressure relative to that of the feed solution.

The term "assisted forward osmosis" (AFO) (or "pressure assisted forward osmosis", PAFO) as used herein refers to the concept of applying a mechanical pressure to the feed side of the membrane to enhance the water flux through synergising the osmotic and hydraulic driving forces.

"Reverse osmosis" (RO) is a process of extracting water through a semi-permeable membrane from a feed solution against a gradient of osmotic pressure, by applying a mechanical pressure that is higher than the osmotic pressure of the feed solution.

"Semi-permeable membrane" is a membrane that will allow certain molecules or ions to pass through it.

"Osmotic pressure" is the pressure that must be applied to prevent the net flow of solvent through a semipermeable membrane from a solution of lower solute concentration to a solution of higher solute concentration.

The osmotic pressure of a solution depends on the amount of particles in the solution. For an ideal solution the osmotic pressure is directly proportional to the molality.

"Osmolality" is a measure of the moles (or osmoles) of osmotic active solutes per kilogram of solvent, expressed as osmole/kg. The osmolality of an ideal solution of a non-dissociated compound equals the molality.

Osmolality is typically measured by freezing point depression. A one osmol/kg aqueous solution has a freezing point of $-1.858°$ C. As an example: a 1 mol solution of e.g. sugar in 1 kg of water lowers the freezing point with $1.858°$ C. whereas the freezing point depression will be obtained by 0.5 mol in 1 kg of water.

"Osmolarity" is a measure of the osmoles of solute per liter of solution.

The "osmotic pressure" can be calculated from the osmolality by using the formula:

$$\pi(\text{bar}) = osmolality\left(\frac{osmole}{L}\right) \times R \times T(K)$$

wherein R is the gas constant (8.3144621 L bar $K^{-1}$ $mol^{-1}$).

"Aquaporin" as used herein refers to selective water channel proteins, including AqpZ and SoPIP2;1 prepared according to the methods described by Maria Karlsson et al. (FEBS Letters 537 (2003) 68-72) or as described in Jensen et al. US 2012/0080377 A1.

"Asolectin" as used herein refers to a soybean lecithin fraction [IV-S] which is a highly purified phospholipid product containing lecithin, cephalin, inositol phosphatides & soybean oil (synonym: azolectin).

"Block copolymer" as used herein refers to membrane forming or vesicle forming di- and tri-block copolymers having both hydrophilic (A or C) and hydrophobic (B) blocks; the diblock copolymers being of the A-B or C-B type which are able to form bilayers and the triblock copolymers being of the A-B-A or A-B-C type that form monolayers by self assembly, where all of the membranes have the hydrophobic layer in the middle. Examples of useful diblock copolymers and examples of useful triblock copolymers are disclosed in U.S. Pat. No. 5,364,633 and the following (all from the supplier Polymer Source):

| Species | Formula | $n_{(hydrophobic)}$ | $n_{(hydrophilic)}$ |
|---------|---------|---------------------|---------------------|
| P7258 | $EO_{48}DMS_{70}$ | 70 | 48 |
| P5809 | $EO_{15}BO_{16}$ | 15 | 16 |
| P8365 | $EO_{25}DMS_8$ | 8 | 25 |
| P7259 | $EO_{48}DMS_{14}$ | 14 | 48 |
| P7261 | $EO_{114}DMS_{14}$ | 14 | 114 |
| P3691B | $MOXA_6DMS_{35}MOXA_6$ | 35 | 12 |
| P8061 | $MOXA_{15}DMS_{67}MOXA_{15}$ | 67 | 30 |
| P9548 | $MOXA_{15}DMS_{119}MOXA_{15}$ | 119 | 30 | where EO-block-DMS-block represents poly(dimethylsiloxane-block-ethylene oxide-block), EO-block-BO-block represents poly(butylene oxide-block-ethylene oxide-block), and MOXA-block-DMS-block-MOXA-block represents poly(2-methyl-oxazoline-block-dimethylsiloxane-block-2-methyloxazoline).

"Thin-film-composite" or (TFC) membranes as used herein refers to a thin film membrane active layer having an additional aquaporin component, said layer being prepared using an amine reactant, preferably an aromatic amine, such as a diamine or triamine, e.g. 1,3-diaminobenzene (m-Phenylenediamine>99%, e.g. as purchased from Sigma-Aldrich) in an aqueous solution, and an acyl halide reactant, such as a di- or triacid chloride, preferably an aromatic acyl halide, e.g. benzene-1,3,5-tricarbonyl chloride (CAS No. 84270-84-8, trimesoyl chloride (TMC), 98%, e.g. as purchased from Sigma-Aldrich) dissolved in an organic solvent where said reactants combine in an interfacial polymerization reaction, cf. U.S. Pat. No. 4,277,344 which describes in detail the formation of a polyamide thin film formed at the surface of a porous membrane support, e.g. a polyethersulfone membrane. More specifically, benzene-1,3,5-tricarbonyl chloride can be dissolved in a solvent, such as a C6-C12 hydrocarbon including hexane (>99.9%, Fisher Chemicals), heptane, octane, nonane, decane etc. (straight chain or branched hydrocarbons) or other low aromatic hydrocarbon solvent, e.g. Isopar™ G Fluid which is produced from petroleum-based raw materials treated with hydrogen in the presence of a catalyst to produce a low odor fluid the major components of which include isoalkanes. Isopar™ G Fluid: Chemical Name: Hydrocarbons, C10-C12, isoalkanes, <2% aromatics; CAS No: 64742-48-9, chemical name: Naphtha (petroleum), hydrotreated heavy (from ExxonMobil Chemical). Alternatives to the reactant 1,3-diaminobenzene include diamines such as hexamethylenediamine etc., and alternatives to the reactant benzene-1,3,5-tricarbonyl chloride include a diacid chloride, adipoyl chloride etc. as known in the art. To make the active layer a thin film composite layer, an additional component, herein aquaporin water channels, that facilitates water transport are added to the reactant solutions before interfacial polymerization takes place. Said component may or may not participate in the reaction, but preferably is inert to the reaction and becomes immobilised in the thin film formed. Herein, the aquaporin water channels are preferably contained in vesicles, such as proteoliposomes and proteopolymersomes, formed from amphiphilic compounds.

"Proteoliposomes" as used herein are vesicles that typically have a lipid to protein ratio (LPR calculated on a mole basis) of between 25 to 500, such as about 100 to about 200.

"Proteopolymersomes" as used herein are vesicles that typically have a polymer to protein ratio (POPR calculated on a molar basis) of between 25 to 500, such as about 50 to about 100 when using a triblock copolymer and a polymer to protein ratio of between 25 to 500, such as about 100 to about 200 when using a diblock copolymer.

"Aquaporin membrane" as used herein refers to a membrane comprising an active layer comprising immobilised aquaporin water channels and a support layer. In said aquaporin membrane the aquaporin water channels are immobilized or more or less embedded or partly embedded in or even supported in or on said active layer. Said active layer is preferably created in close contact with a support layer, such as a typical polysulfone or polyether sulfone support membrane.

In one embodiment, the membrane comprises an active layer being a thin film composite (TFC) layer comprising aquaporin water channels.

Formation of a separation layer in the form of a thin film layer as known in the art onto the surface of a support membrane (flat sheet or hollow fiber) results in changes to the water transport mechanism. Instead of water transport taking place by normal diffusion through the pores of the support membrane, another type of water transport takes place through the thin film layer as is known from this type of reverse osmosis membranes, where membrane permeability is limited. The nonporous nature of the thin film separating layer results in transport of water requiring "jump diffusion" as described in Kotelyanskii et al. 1998. Thus, thin film modification of water membranes have mainly found use in reverse osmosis, where a hydrostatic pressure is required to force the water through the membrane, and the obtained advantage lies in the improved separation of unwanted solutes in the water to be filtered. These conventional membranes for reverse osmosis have effectively 100-200 nm thick non-porous layers supported by a porous material. Water permeation in these membranes occurs as a diffusion process through the non-porous layer established via the appearance and disappearance of interstitial spaces. The active layer used in the systems herein is further improved relative to the prior art thin film membranes by having aquaporin water channels incorporated in the thin film layer making it a thin film composite (TFC) layer. The incorporation of aquaporins have the added benefit of providing a selective water transport through its pores having a diameter of only 2.4 Å at its narrowest passage (AqpZ pore, cf. Wang et al. 2005) where an efficient single file water transport takes place.

In a further embodiment the aquaporin water channels are incorporated in vesicles before incorporation into the TFC layer. In a further embodiment the vesicles into which the aquaporin water channels are incorporated are liposomes or polymersomes. In a further embodiment liposomes are prepared from lipids such as DPhPC, DOPC, mixed soy bean lipids, asolectin or *E. coli* mixed lipids. In a further embodiment the polymersomes comprise triblock copolymers of the hydrophile-hydrophobe-hydrophile (A-B-A or A-B-C) type or diblock copolymers of the hydrophile-hydrophobe type (A-B).

Said aquaporin water channels are preferably AqpZ channels, but, in principle, all water selective aquaporins, e.g. such as aquaporin Z (AqpZ), Aqp1, G1pF or SoPIP2;1, are useful in the invention. In a further embodiment the aquaporin water channels are AqpZ channels or SoPIP2;1 water channels.

In a further embodiment TFC layer is formed through interfacial polymerization of an aqueous solution of a di- or triamine with a solution of di- or triacyl halide in an organic solvent, and wherein the aquaporin water channel vesicles are incorporated in said aqueous solution.

The membrane may be manufactured at described by Zhao, Y. et al (2012).

"Flow cell" as used herein represents a filter (or membrane) module with a feed compartment and a non-feed compartment. The flow cell may be adapted for RO, e.g. having a feed solution inlet and a permeate outlet, or the flow cell may be adapted for FO where an inlet and an outlet for feed solution is fitted on one side of the cell to allow fluid communication with the membrane, and an inlet and an outlet for draw solution is fitted on the opposite side of the cell to allow fluid communication with the opposite side of the membrane. Examples of useful flow cells include the following from Sterlitech Corp, WA, US. (http://www.sterlitech.com):

FO cell: CF042-FO (Delrin Acetal or Acrylic)
RO cell: CF042 Crossflow Cell
Membranes of size 5.5 cm×11 cm fit into the CF042 cells.
FO/RO cell: SEPA CF II
This cell can have an RO top or an FO top. Membranes of size 13.5 cm×19 cm fit into the SEPA CF II cell.

"Impaired ground water" is used herein synonymously with the terms "contaminated ground water" and "polluted ground water", all of which terms are well known to the person skilled in the art.

Cleaning of the Membrane in the Systems

Membrane fouling can cause flux decline and affect the quality of the water extraction process. The degree of fouling may be controlled such as by measuring flux decline as determined by flow rates of feed and draw solutions at specific points in the water extraction system. The systems for water extraction may also include means for maintenance purposes, such as means for introducing air or a cleaning solution or such as for the utilisation of physical and/or chemical cleaning techniques. Physical methods for cleaning the membrane of the water extraction system include forward and reverse flushing, backwashing, air flushing (also called air scouring) and sponge ball cleaning (Al-Amoudi 2007). In one embodiment, the water extraction system may be cleaned by introducing bubbles into the cleaning solution for air scouring.

With respect of chemical cleaning, Al-Amoudi et al. (2007) gives an overview of cleaning systems for nanofiltration membranes and Porcelli et al. (2010) gives a review of chemical cleaning of potable water membranes. One example of cleaning reagent is citric acid that can provide buffering and has chelating abilities. Further citric acid can disrupt biofilm formation by removing minerals from foulant layers. A second example of cleaning reagent is EDTA (ethylenediamine tetraacetic acid) which provides chelation capacity for metals such as calcium and dispersed minerals in general.

Robust Operation Conditions

The water extraction system of the invention is useful under varied pH and temperature conditions due to the robustness of the aquaporin membrane, which can tolerate pH values as low as 2 and as high as 11 and temperatures as high as 65° C. and as low as 10° C. The water flux becomes reversibly reduced during very high and very low pH and temperature feed values, so that the membrane regains its high initial performance, cf. the tables below:

Results for FO experiments using TFC-AqpZ membrane in a CF042 cell at high and low feed pH:

| Amphiphile | n | $J_w$ (L/m²h) | $J_s$ (g/m²h) | $J_s/J_w$ | $R_{Ca}$ (%) |
|---|---|---|---|---|---|
| P8061 - pH 6.3 | 14 | 12.60 ± 1.21 | 3.88 ± 0.83 | 0.31 | 99.80 ± 0.22 |
| P8061 - pH 2.0 | 3 | 5.60 ± 0.79 | — | — | — |
| P8061 re-run pH 6.3 | 3 | 12.22 ± 0.95 | 4.32 ± 0.26 | 0.35 | 99.71 ± 0.19 |
| P8061 - pH 11.0 | 3 | 7.44 ± 0.57 | — | — | — |
| P8061 re-run pH 6.3 | 3 | 11.49 ± 2.42 | 4.17 ± 0.49 | 0.36 | 99.55 ± 0.16 |

The results in the table above clearly shows that the FO system is pH sensitive and pH tolerant and that the membrane performance as measured by water flux ($J_w$), reverse salt flux ($J_s$) and calcein rejection ($R_{Ca}$) is reversible at neutral pH. The calculated $J_s/J_w$ values are based on the average values and generally shows a consistent membrane performance at all pH values tested. Thus, it is a further purpose of the invention to provide a water extraction system having a stable performance in the pH range of from about pH 2 to about pH 11 as defined by the $J_s/J_w$ values. In a special aspect the invention provides a water extraction system for use in a low pH process, such as a low pH forward osmosis process, such as a process at a pH below 6, 5, 4 or 3. In a further special aspect the invention provides a water extraction system for use in a high pH process, such as a high pH forward osmosis process, such as a process at a pH above 8, 9, 10 or 11.

In addition, the water extraction system of the invention is heat tolerant. However, it was found that operation at both 10° C. and 65° C. has an impact FO performance. At 65° C. high water fluxes are accompanied by higher reverse salt flux values. Operation at 10° C. results in a lower water flux and a high retention. Operation at 50° C. obtains water fluxes and salt rejection values that are comparable to the performance standards of the reference system at 22° C. for a TFC-aquaporin membrane using P8061 as amphiphilic vesicle forming material (amphiphile) and in a system where the feed solution contains dissolved calcein as a trace material. Finally, it was found that membrane exposure to 10° C. and 65° C. for about 1200 minutes does not cause any damage to the membrane and that successive standard FO operation of the system was not negatively influenced. Results are given in the table below:

Results for FO experiments using TFC-AqpZ membrane in a CF042 cell at high and low feed temperatures:

| Amphiphile | n | $J_w$ (L/m²h) | $J_s$ (g/m²h) | $J_s/J_w$ | $R_{Ca}$ (%) |
|---|---|---|---|---|---|
| P8061 Reference - 22° C. | 14 | 12.60 ± 1.21 | 3.88 ± 0.83 | 0.31 | 99.80 ± 0.22 |
| P8061 - 65° C. | 3 | 22.09 ± 3.93 | 7.49 ± 3.4 | 0.33 | 99.75 ± 0.29 |
| P8061 Re-run - 22° C. | 1 | 11.55 | 4.08 | 0.35 | 99.81 |
| P8061 - 50° C. | 3 | 20.16 ± 6.20 | 3.67 ± 2.41 | 0.18 | 99.92 ± 0.06 |
| P8061 Re-run - 22° C. | 1 | 12.37 | 2.43 | 0.36 | 99.70 |
| P8061 - 10° C. | 3 | 7.02 ± 0.16 | 2.43 ± 0.89 | 0.34 | 99.95 ± 0.02 |
| P8061 Re-run - 22° C. | 1 | 13.16 | 3.30 | 0.25 | 99.95 |

The results in the table above clearly shows that the FO system is heat sensitive and heat tolerant and that the membrane performance as measured by water flux ($J_w$), reverse salt flux ($J_s$) and calcein rejection ($R_{Ca}$) is reversible at room temperature. In addition, the calculated $J_s/J_w$ values based on the average values in the above table show that the membrane performance is unaffected by changes in temperature in the interval from 10 to 65° C. Thus, it is a further purpose of the invention to provide a water extraction system having a stable performance in said temperature interval as defined by the $J_s/J_w$ values. In a special aspect the invention provides a water extraction system for use in a high temperature process, such as a high temperature forward osmosis process, such as a forward osmosis process at a temperature above 30, 40, 50 or 60° C.

The present invention is further illustrated by the following examples, which should not be construed as limiting the scope of the invention.

EXPERIMENTAL SECTION

Preparation of Vesicles (Liquid Membrane)
Preparation of 1 mg/mL Asolectin proteoliposomes, and lipid to protein ratio (LPR) 200 using AqpZ Mw 27233 according to the following protocol:
1. Fill a 50 mL glass evaporation vial with 5 mL of a 2 mg/mL stock solution of asolectin (mW 786.11 g/mol, Sigma) in CHCl$_3$.
2. Evaporate the CHCl$_3$ using a rotation evaporator for at least 2 h to complete dryness.
3. Add 0.8 mL of buffer solution (1.3% octylglucoside (OG) in PBS pH 7.4) to rehydrate the film obtained in the evaporation vial in step 2.
4. Shake the vial at maximum rpm on a platform shaker (Heidolph orbital platform shaker Unimax 2010 or equivalent) until the lipid is dissolved.
5. Add 1.73 mg of AqpZ in a protein buffer containing Tris pH8, glucose and OG, 10 mg/mL, and rotate vial for 15 min at 200 rpm, the AqpZ being prepared according to description above.
6. Slowly add 9.03 ml PBS (pH 7.4 without OG), and shake vial for 15 min at 200 rpm.
7. Freeze/thaw the combined solution/suspension on dry ice/40° C. water bath for three times to eliminate possible multilamellar structures.
8. Add 250 mg of hydrated Biobeads (SM2 from BioRad) and rotate vial for 1 h at 200 rpm at 4° C. to adsorb detergent (OG).
9. Add further 250 mg of hydrated Biobeads and rotate vial for 2 to 3 days at 200 rpm at 4° C.
10. The Biobeads with adsorbed OG are then removed by pipetting off the suspension.
11. Extrude the obtained suspension for about 11 times through a 200 nm polycarbonate filter using an extruder, such as from at least 1 time and up to about 22 times to obtain a uniform proteoliposome suspension in the form of a vesicles (a liquid membrane) suspension.

Instead of using BioBeads, the detergent can be removed on a typical resin column, such as an Amberlite XAD-2.

Protocol for 1 mg/ml proteo-polymersomes, protein to polymer ratio (POPR) 50 Polyoxazoline Based Triblock Copolymers, Poly(2-methyl oxazoline-b-dimethyl siloxane-b-2-methyl oxazoline), Moxa 30: DMS 67, Mw 7319 (P8061 purchased from Polymer Source™, Quebec, Canada), AqpZ Mw 27233
1. Fill a 50 ml glass evaporation vial with 5 ml of a 2 mg/ml stock solution of P8061 in CHCl3.
2. Evaporate the CHCl3 using a rotation evaporator for at least 2 h to complete dryness.
3. Add 3.0 mL of buffer solution (1.3% O.G.; 200 mM Sucrose; 10 mM Tris pH 8; 50 mM NaCl) to rehydrate the film obtained in the evaporation vial in step 2.

4. Shake the vial at 200 rpm on a platform shaker (Heidolph orbital platform shaker Unimax 2010 or equivalent) for 3 hours to obtain dissolution of the copolymer.
5. Add 75 μL of AqpZ in a protein buffer containing Tris, glucose and OG, and rotate vial over night at 200 rpm and 4° C.
6. Add 6.88 ml buffer (10 mM Tris pH 8; 50 mM NaCl) slowly while mixing up and down with pipette.
7. Add 180 mg hydrated Biobeads and rotate for 1 h at 200 rpm.
8. Add 210 mg hydrated Biobeads and rotate for 1 h at 200 rpm.
9. Add 240 mg hydrated Biobeads and rotate O.N. at 200 rpm 4° C.
10. Add 240 mg hydrated Biobeads and rotate O.N. at 200 rpm 4° C.
11. The Biobeads with adsorbed OG are then removed by pipetting off the suspension.
12. Extrude the suspension for about 21 times through a 200 nm polycarbonate filter using an extruder, such as from at least 1 time and up to about 22 times to obtain a uniform proteopolymersome suspension (vesicles) suspension.

TFC Active Layer Preparation:
Materials:
Apolar solvent: Hexane or an isoparaffin solvent, such as Isopar G, ExxonMobil Chemical
TMC: 1,2,5 Benzenetricarbonyltrichloride from Aldrich 147532
MPD: m-Phenyldiamine from Aldrich P23954
Vesicles: Proteopolymersomes or proteoliposomes prepared as described above, e.g. using p8061-MOXZDMSMOXZ (Poly(2-methyloxazoline-b-dimethylsiloxane-b-2-methyl-oxazoline) from Polymer Source Inc., Quebec, Canada, with AQPZ (POPR 50) Support membrane: MICROPES 1FPH or 2FPH manufactured by Membrana GmbH.

Interfacial Polymerization:

Interfacial polymerization is a polymerization reaction that is taking place at the interface between two immiscible liquids with different monomers dissolved. Here, MPD is dissolved in water and vesicles are added. The porous PES support membrane, e.g. a MICROPES 1FPH or 2FPH membrane from Membrana GmbH is cut in rectangular shape, e.g. 5.5 cm×11 cm, 13.5 cm×19 cm, or 20 cm×25 cm, and soaked in the aqueous solution and the surface is dried just enough to have a dry surface with aqueous solution filled pores. TMC is dissolved in an apolar solvent (hexane or Isopar™) and applied to the surface of the semidried soaked support membrane. The MPD and TMC react at the interface between the two liquids and form a highly cross-linked network of aromatic polyamide. TMC reacts with water to give a carboxylic acid group and HCl, thus the TMC is broken down in the aqueous phase. MPD reacts readily with TMC, thus it does not diffuse far into the apolar solvent. The resulting layer is a highly cross-linked aromatic polyamide film embedded in the support membrane surface with a thickness of approximately 100-700 nm. The vesicles become immobilized by being trapped or embedded in the cross-linked polyamide film.

Figure 4:
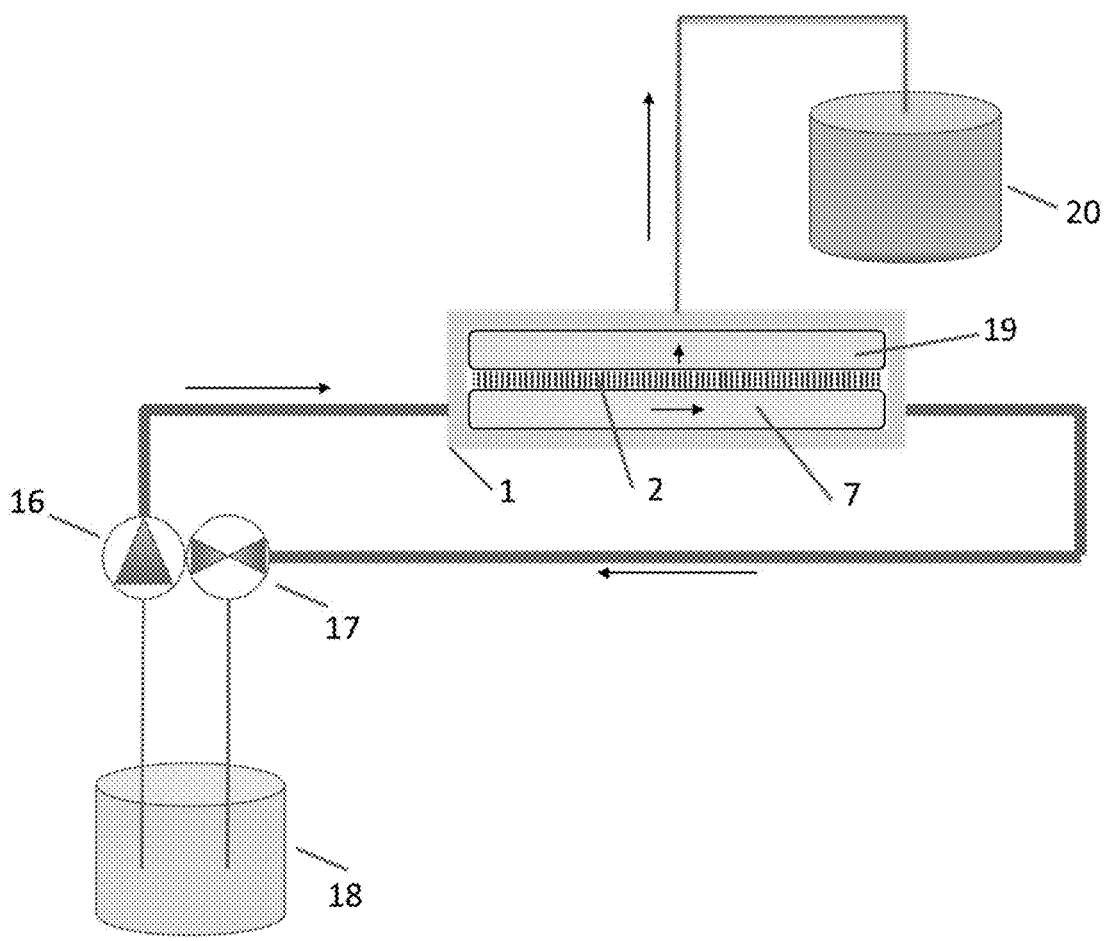
FIG. 4 shows a schematic diagram of a Reverse Osmosis (RO) system, wherein: (18) is the feed tank; (16) is a pump; (17) is a valve; (19) is the permeate and (20) is the permeate tank. The flow from the pump through the flow cell and back to the valve is a pressurized flow.

Example 1. System for Removal of Boron Contamination in a Freshwater Source Using FO and RO FIG. 4 shows a system for water extraction with boron removal using a Washguard SST pump (16) and an osmotic cell (Sterlitech CF042) for RO filtration, where said cell holds a 5.7 cm×11.3 cm TFC-AqpZ membrane prepared as described herein, and wherein a boron contaminated fresh water feed source created by dissolving boric acid to about 5 mg/L B in tap water having a mean content of 187 μg/L B, 0.20 μg/L As, 113 mg/L Ca, pH=7.5 (source: HOFOR, Copenhagen 2011) is filtered through said membrane during RO operation mode at a pressure of 125 psi. The resulting permeate can be sampled for ICP-MS boron elemental analysis, e.g. according to Nagaishi & Ishikawa (2009), giving a calculated rejection range based on the obtained analytical data of from about 45% to about 55% rejection comparable to the results obtained by Kim et al. 2012.

FIG. 2 shows a system for water extraction with boron removal using the same feed source as in the RO experiment above and a draw solution of 35 g/L NaCl in tapwater (same tap water source as for the feed) in a closed circuit. The FO system uses a Sterlitech CF042P osmotic cell adapted for FO mode, where said cell holds a TFC-AqpZ membrane prepared as described herein, cf. the figure. The FO system is operated with counter-current flow velocities of 50.03 ml/min corresponding to 0.85 cm/s, and both active side of membrane against draw and active side of membrane against feed solutions were tested. After 1300 min operation samples for ICP-MS boron elemental analysis were taken from the draw solutions giving a calculated rejection range based on the obtained analytical data of from about 60% to about 85% representing potential for improved rejection during FO compared to the results published by Kim et al. 2012.

Tabulated results from 10 FO experiments with membranes having an active area of 8.5 cm×3.9 cm prepared as described above and a feed solution comprising 5 mg/mL of boron in the form of boric acid in tapwater adjusted vs. 2M NaCl draw solution:

Active membrane layer on the non-feed side (against draw solution) cf. FIG. 1C

| Date & configuration | Jw/LMH 900 min | Js/GMH 900 min | B Rejection at app. 1300 min |
|---|---|---|---|
| 220812 AL-DS | 11.83 | 1.99 | 62% |
| 300812 AL-DS | 11.39 | 2.02 | 65% |
| 091012 AL-DS | 9.1 | 1.64 | 74% |
| 101012 AL-DS | 9.31 | 1.09 | 76% |
| 221012 AL-DS | 10.54 | 5.66 | 53% |
| Mean Value | 10.43 | 2.48 | 66% |
| Std. | 10% | 66% | 13% |

Active membrane layer on the feed side (against feed solution) cf. FIG. 1C

| Date & configuration | Jw/LMH 900 min | Js/GMH 900 min | B Rejection at app. 1300 min |
|---|---|---|---|
| 220812 AL-FS | 12.07 | 3.41 | 64% |
| 091012 AL-FS | 6.8 | 1.68 | 82% |
| 101012 AL-FS | 8.24 | 1.15 | 86% |
| 221012 AL-FS | 9.19 | 1.75 | 77% |
| Mean Value | 9.08 | 1.9975 | 77% |
| Std. | 21% | 42% | 11% |

In these experiments the FIG. 1B membrane configuration showed a higher rejection % and is thus advantageous.

In addition, 5 reverse osmosis experiments with active membrane layer on the side of a feed solution of 5 mg/ml Boron as boric acid in tapwater, flow 0.25 m/s and applied pressure of 8.62 bar showed a mean value of boron rejection of 50%±8%.

Example 2. System for Removal of Arsenic Contamination in a Freshwater Source Using FO and RO The same RO system as described in Example 1 was used except that an artificially created feed solution of 5 mg/L As (arsenic acid dissolved in MilliQ water and adjusted to pH 9.5 using 1N NaOH) is filtered through said membrane during RO operation mode at a pressure of 125 psi. The resulting permeate can be sampled for ICP-MS arsenic elemental analysis, e.g. as described by Grosser (2010), giving a calculated rejection range based on the obtained analytical data of about 100% rejection.

The same FO system as described in Example 1 was used except that a feed solution of 5 mg/L As in MilliQ water, pH 9.5, and a draw solution of 2M NaCl in MilliQ water was used. After 1300 min operation samples for arsenic elemental analysis were taken from the draw solutions for ICP-MS analysis. The results show that a calculated arsenic rejection based on the obtained analytical data of about 100% can be obtained using FO filtration (both when using the active side of the TFC membrane against the draw solution and using the active side of the TFC membrane against the feed solution).

Tabulated results from 10 FO experiments with membranes having an active area of 8.5 cm×3.9 cm prepared as described above and a feed solution comprising 5 mg/L of arsenic in the form of $As_2O_3$ in milliQ water adjusted to pH 9.5 vs. 2M NaCl draw solution:

Active membrane side against non-feed (draw), cf. FIG. 1C

| Date & configuration | Jw/LMH 900 min | Js/GMH 900 min | As Rejection at app. 1300 min |
|---|---|---|---|
| 240812 AL-DS | 11.5 | 4.69 | 103% |
| 161012 AL-DS | 15.37 | 4.81 | 113% |
| 171012 AL-DS | 15.01 | 7.61 | 98% |
| 241012 AL-DS | 14.97 | 8.91 | 102% |
| 251012 AL-DS | 13.01 | 4.94 | 94% |
| Mean Value | 13.97 | 6.192 | 102% |
| Std. | 11% | 28% | 6% |

Active membrane layer against feed, cf. FIG. 1B

| Date & configuration | Jw/LMH 900 min | Js/GMH 900 min | As Rejection ca 1300 min |
|---|---|---|---|
| 240812 AL-FS | 10.81 | 5.81 | 102% |
| 161012 AL-FS | 11.3 | 2.67 | 102% |
| 171012 AL-FS | 14.28 | 4.01 | 102% |
| 241012 AL-FS | 11.6 | 1.67 | 105% |
| 251012 AL-FS | 11.6 | 2.31 | 95% |
| Mean Value | 11.92 | 3.294 | 101% |
| Std. | 10% | 45% | 3% |

In addition, 5 reverse osmosis experiments were run where the active side of the same type of membrane was positioned against the feed solution comprising 5 mg/L of arsen in the form of $As_2O_3$ in milliQ water adjusted to pH 9.5, flow 0.25 m/s and applied pressure of 8.62 bar. These experiments consistently showed a mean value of arsenic rejection of 98%±1%.

Example 3. System Comprising an FO Concentrator Module, e.g. for Peptides

Figure 7:
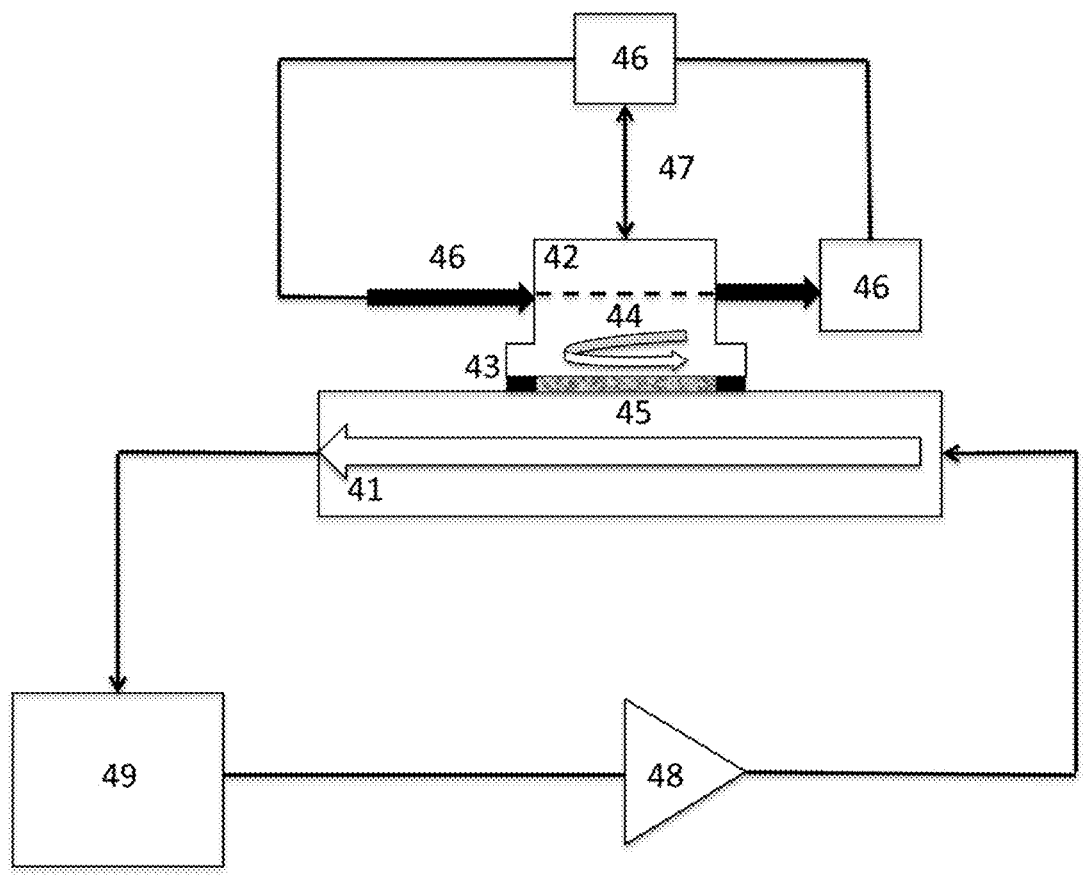
FIG. 7 shows a schematic diagram of a FO concentrator, wherein (41) is the base unit containing a flow inlet and flow outlet to ensure an optimal draw solution flow profile beneath the membrane (45); (42) is the disposable top unit; the membrane (45) is secured and sealed to the top unit together with an additional seal (43) to the base unit; (44) is an optional flow generator to stir the solution in the top unit; (46) is an inline monitoring system to monitor and continuously display the degree of concentration in the top unit feed solution, e.g. the volume and weight can be inspected visually; (47) is the feedback loop mechanism designed to stop the concentration process once the desired concentration is reached; (48) is a pump to recirculate the draw solution; and (49) is a disposable draw solution pouch containing customized draw solution for different concentration processes.

Method:

FO module is prepared by the following steps:
1. water tight fastening, such as gluing with silicone glue or otherwise clamped tight, of a plastic measuring cylinder (such as having a diameter of 1 cm and the like depending on volume to be up-concentrated) to a Plexiglas surface with a corresponding hole of area 0.5 cm2 or 3.14 cm2, where the feed solution will be exposed to the membrane.
2. A mesh support is glued immediately underneath.
3. A TFC-AqpZ membrane, such as prepared using 1 FPH support membrane and P8061 amphiphilic copolymer for the polymersomes, was prepared as described above, where active side on top is glued under the support or, alternatively, water tight fastened with O-ring.
4. Optionally, a rubber gasket may be glued after the membrane.
5. An additional rubber gasket can be added as a cushion when the top part is assembled with the bottom part where the tubing is placed, cf. FIG. 7 or 8 below.
6. The module is now connected to a pump, such as a peristaltic pump where draw solution is recirculated through the system, typically at flow speed of 40 mL/min. An osmotic gradient created by using 2M NaCl in MilliQ water as draw solution drives the movement of water from the feed solution in the measuring cylinder to the draw.

Detection of Feed Solute (Peptide or Protein or Other Sample):

In this example a concentrated feed solution of the custom made peptide GGGSGAGKT (available from Caslo Laboratory as a lyophilized trifluoroacetate salt, molecular weight measured by MS of 690.71, purity 98.87%) or of the amino acid L-lysine (from Sigma Aldrich, molecular weight 146.1 g/mol, 97% purity)) was mixed with equal volumes of LavaPep kit (from gelcompany.com, the kit binds to lysine residues in peptides and is used herein experimentally also to detect the free amino acid) and incubated for 1 h in the dark at room temperature. Detection of peptides and L-lysine is done on QuBit with the setting "ssDNA". Detection range of ssDNA on QuBit: excitation: 400-490 nm, 500-645 nm; emission: 570-645 nm.

Generation of Standard Curve:

Peptide/lysine in 6 different concentrations ranging from 1000 to 1 µg/mL in 9.3×TES buffer is analysed, the concentrations being suitable due to feed getting concentrated about 2 to 6 times during the up-concentration.

Quantification: 10 µL of concentrated solution (2 to 5× conc.)+90 µL 10×TES buffer to end up at 9.3× buffer in the dilution+100 µL kit.

Detection range of LavaPep kit: excitation: 405-500 nm (green 543, 532 nm, blue 488 nm, violet 405 nm or UVA); emission: max 610 nm (band pass or 560 long pass)

Excitation: 540+−10 nm; emission: 630+−10 nm

The concentrated feed solution of the peptide/lysine is detected and measured as follows:
1. Start feed: about 50 µg/mL peptide or lysine in 1×TES buffer
2. Run assay
3. Collect concentrated solution
4. 10 µg/mL conc. peptide sol.+90 µg/mL 10×TES buffer+100 µg/mL kit
5. Incubation in the dark for 1 h at room temperature
6. Measure fluorescence counts in QuBit
7. Read concentration from standard curve Solutions:

Feed: 200 µg/mL L-lysine (amino acid example), or 50 µg/mL-500 µg/mL of peptide in 1×TES buffer, or 500 µg/mL of bovine serum albumin (BSA) used as a protein example in PBS buffer (0.303 Osm)

Draw solution: 2M NaCl (200 mL) in MilliQ water
Peptide, protein and L-lysine kit: LavaPep kit (fluorescent compound: epicocconone, binds to lysine, and is used for quantification of lysine residue in peptide). Preferably, Lysine (and other amino acids) may be quantified using HPLC.

Results for the up-concentrations are as follows
Experimental conditions: A large scale experiment using 1 L of feed and 1 L of draw solutions in the Sterlitech CF042 chambers
Feed: 200 µg/mL L-lysine in 1×TES buffer
Draw: 2M NaCl
Operation time: about 1175 min
End concentration L-lysine is concentrated about 7 times
Experimental conditions: A large scale experiment as above
Feed: 200 µg/mL L-lysine in 1×TES buffer
Draw: 2M NaCl
Operation time: about 1175 min
End concentration L-lysine is concentrated about 6 times
Experimental conditions: small scale, 1 mL
Feed: 50, 200 or 500 µg/mL GGGSGAGKT in 1×TES buffer
Draw: 2M NaCl
Operation time: about 1175 min The upconcentration of the volumes and peptide concentrations are in the table below:

| Concentration of feed, start [µg/mL] | Volumen upconcentration [times] | Peptide upconcentration [times] |
|---|---|---|
| 50 | 2.3 | 1.9 |
| 200 | 5 | 6 |
| 500 | 4.3 | 4.8 |

Conclusion: the results clearly show that during less than 20 hours of forward osmosis operation in the system the feed L-lysine solutes can be concentrated up to about 6 to 7 times, and for the feed peptide solutions these can be concentrated up to 6 times with the feed volume being concentrated in the same order of magnitude.

Example 4. Treatment of the Membrane with Citric Acid

Membranes were prepared as described in the experimental section above and were tested for robustness against treatment with citric acid. The membranes were submerged in a 0.3% citric acid solution and left soaking for 15 minutes (n=3).

Before and after the soaking process the membranes were run in FO mode (with 5 µM calcein feed and 2 M NaCl as draw solution) in a CF042 flow cell for 900 min.
The results of the tests are in the table below:

| | $J_w$ [L/m$^2$h] | $J_{s,\,total}$ [g/m$^2$h] | $R_{calcein}$ [%] |
|---|---|---|---|
| Before treatment (n = 3) | 10.33 | 2.26 | 99.94 |
| After treatment (n = 3) | 11.43 | 3.40 | 99.76 | wherein $J_w$ is the water flux through the membrane,
$J_{s,\,total}$ is the reverse salt flux through the membrane and
$R_{calcein}$ is the calcein rejection.

As can be seen from the table, the treatment does not influence the water flux negatively and the calcein rejection is maintained at a very high level.

Example 5. Treatment of the Membrane with EDTA

Membranes were prepared as described in the experimental section above and were tested for robustness against treatment with EDTA. The membranes were submerged in a 0.8% EDTA solution and left soaking for 15 minutes (n=3).
Before and after the soaking process the membranes were run in FO mode (with 5 µM calcein feed and 2 M NaCl as draw solution) in a CF042 flow cell for 900 min.
The results of the tests are in the table below:

| | $J_w$ [L/m$^2$h] | $J_{s,\,total}$ [g/m$^2$h] | $R_{calcein}$ [%] |
|---|---|---|---|
| Before treatment (n = 3) | 10.06 | 2.23 | 99.94 |
| After treatment (n = 3) | 10.99 | 3.51 | 99.00 | wherein $J_w$ is the water flux through the membrane,
$J_{s,\,total}$ is the reverse salt flux through the membrane and
$R_{calcein}$ is the calcein rejection.
As can be seen from the table, the treatment does not influence the water flux negatively and the calcein rejection is maintained at a very high level indicating an intact membrane.

Example 6. Water Extraction System for FDFO

In this example the principle of Fertilizer Drawn Forward Osmosis (FDFO) was tested in a forward osmosis water extraction system according to the present invention with the objective of studying rejection rates of typical plant nutrient salts contained in fertilizer and achievable water flux values.
Protocol:
A concentrated nutrient solution of 66.62 g/L was prepared by dissolving in water e.g. tap water or MilliQwater, a dry NPK granulate from Danish Agro having the following composition: total N 14.0%, nitrate-N 5.7%, ammonium-N 8.3%, phosphorus (citrate and water soluble) 3.0%, Potassium (water soluble) 15.0%, Magnesium total 2.5%, sulfur total 10.0% and boron total 0.02%.
The resulting solution can be used as the draw source in a combined FDFO/desalination system, cf. FIG. 3. Alternatively, a commercial concentrated liquid plant nutrient solution, Blomin (The Scotts Company (Nordic), Glostrup DK) can be used. This nutrient solution consists of following nutrient salt composition and concentration: nitrogen (N)—4.4%; Phosphorus (P)—0.9%; potassium (K)—3.3%; Boron (B)—0.0002%; copper (Cu)—0.006%; iron (Fe)—0.02%; Manganese (Mn)—0.008%, Sulfur (S)—0.0003%; Molybdenium (Mo)—0.0002%; and Zinc (Zn)—0.004%.
With reference to FIG. 3 the system comprises a seawater feed source (10), the water being sampled from Øresund close to the coast at Tuborg Harbour, Copenhagen, said water having an approximate salinity of about 8.7 g/L; (13) is a contained with the concentrated fertilizer solution prepared as described above (optionally fitted with a magnetic stirrer or the like); (1) is a Sterlitech CF042 flow cell with a TFC-AqpZ membrane (active area 0.003315 m2) prepared as described in the experimental section above using P8061 copolymer; (12) is a container with the partly diluted fertilizer solution which can be re-circulated to achieve higher degree of dilution; (14) is the additional freshwater tank (normal tap water can be used) for final adjustment of the degree of dilution of the fertilizer solution; (11) is the concentrated feed stream, e.g. up-concentrated seawater; (15) is the diluted fertilizer solution ready for use. The system will initially run for about 900 min and is expected to result in a sufficiently diluted plant nutrient solution ready for use or ready for use after further dilution, cf. FIG. 3 and explanations to FIG. 3 herein.

Example 7. A Water Extraction System with Separation of Urea from RO Permeate in Dairy Industries With reference to FIG. 4 the system comprises a feed tank (18) with dairy process water having between 45 to 75 mg/L total N corresponding to about 110 mg/L urea; (16) is a pump; (17) is a valve; (19) is the permeate and (20) is the permeate tank. The flow from the pump (Washguard SST) through the Sterlitech CF042 flow cell and back to the valve is a pressurized flow of 125 psi and cross flow speed 0.26 m/s; the remaining flows are not pressurized flows. The permeate content of urea is expected to be reduced by at least 50%.

Figure 5:
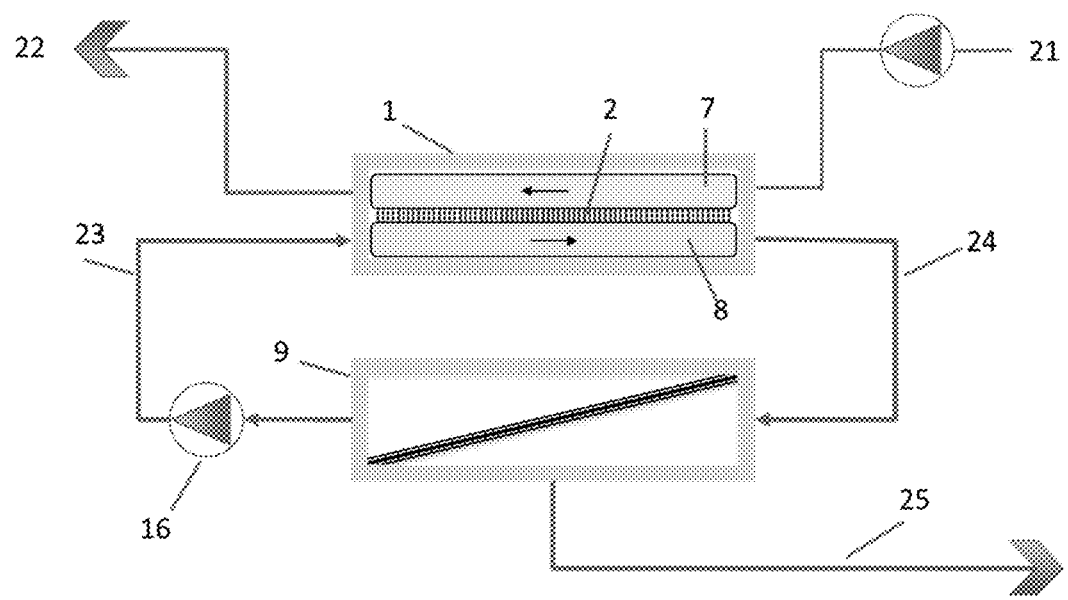
FIG. 5 shows a schematic diagram of a Forward Osmosis (FO) system for desalination with regeneration of the draw solution to extract the product water, wherein (21) is the feed stream, e.g. seawater; (1) is the flow cell with the membrane (2); (22) is the concentrated feed stream; (23) is the concentrated draw solution; (8) the draw solution in fluid communication with the flow cell; (24) the diluted draw solution; (9) the draw solution recovery system; and (25) the desalinated product water, free of draw solution solutes.

With reference to FIG. 5 the system comprises a feed stream (21) having the same composition as above in (18); (1) is the Sterlitech CF042P flow cell with the aquaporin membrane (2) prepared as described in the experimental section above; (22) is the concentrated feed stream; (23) is the concentrated draw solution; (8) the draw solution, e.g. 35 g/L NaCl in tapwater corresponding to typical Kattegat salinity, in fluid communication with the flow cell; (24) the diluted draw solution; (9) the draw solution recovery system; and (25) the desalinated product water free of draw solution solutes. Both feed and draw streams are pumped through the flow cell in counter-current mode at a flow speed of 50.03 ml/min. The resulting urea rejection in this system is expected to be about 75%.

Example 8. A Water Extraction System for Storage of Renewable Energy

This example shows the use of the water extraction system for storing energy from renewable sources, such as energy from sunlight, wind, tides, waves and geothermal heat (i.e. green energy). These energy sources are often intermittent in their nature and there is a high demand for systems for storing such energy.

The storage of energy as a salt gradient as described in this example is comparable with the commonly used process, wherein water is pumped to a higher level location, such as mountains during excess of electrical energy. When the demand of electrical energy is higher than the production capacity, the potential energy of the water is used to drive a turbine. Whereas this known technology is easy to apply in mountain regions it cannot be applied in low level areas or off shore.

With the system according to this Example, energy generated by (off shore) windmills, wave power, solar cells or any other renewable energy source can be stores as salt gradients.

Figure 11:
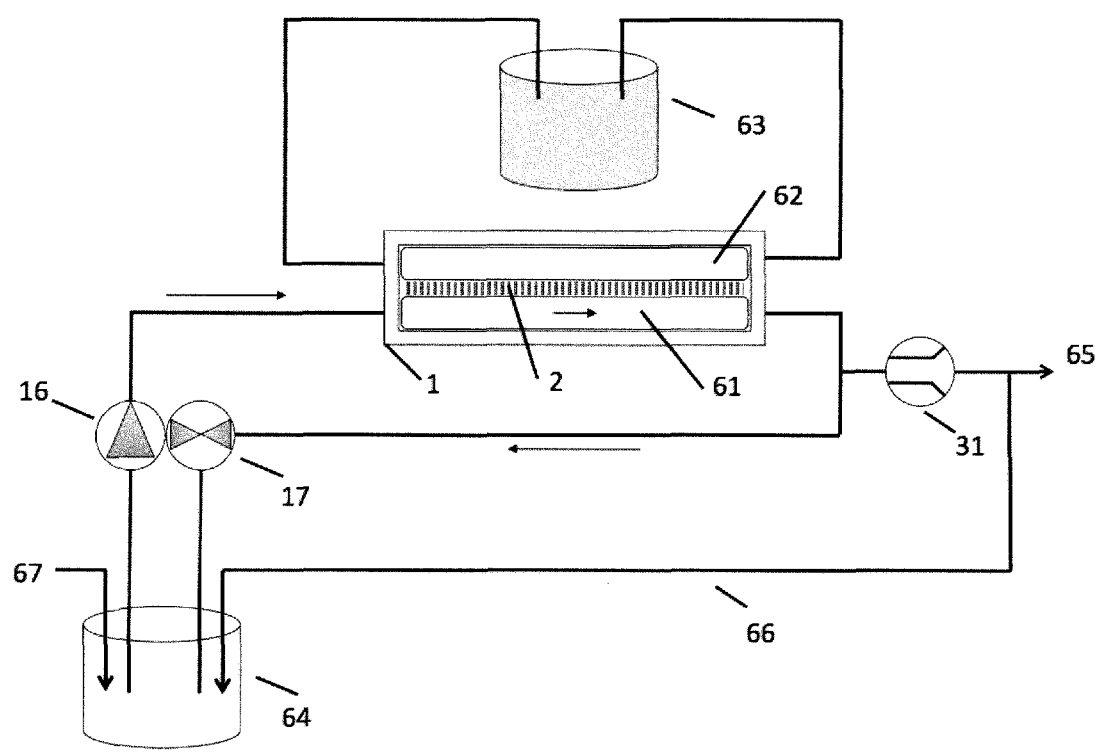
FIG. 11 shows a schematic diagram of a combination of a Reverse Osmosis (RO) system for storing energy from renewable sources by concentration of a salt solution combined with a pressure retarded osmosis (PRO) system for creating energy by dilution of the concentrated solution, wherein (1) is the flow cell with the membrane (2); (61) is the salt solution side; (62) is the desalted water side; (63) is the desalted water tank; (16) is a pump; (17) is a valve; (64) is the salt solution tank; (31) is a turbine to generate power; (65) is an outlet of depressurized diluted salt solution; (66) is a return stream of depressurized diluted salt solution; and (67) is an inlet of fresh salt solution.

With the reference to FIG. 11, if the renewable energy source produces more electrical power than the grid can take up, the energy can be used to concentrate an aqueous solution, such as seawater or even waste water by the process of reverse osmosis. All that is needed is a reservoir for salt solution (64) (which in its simplest form could be the ocean), a reservoir for the desalted water (63), a pressure delivering pump (16) run by the surplus electrical power, and a flow cell (1) with the osmosis membrane (2). The pressure gradient forces the freshwater (desalted seawater) to be pressed through the membrane, leaving behind concentrated saltwater.

At times, where more electrical power is needed than the renewable energy source can generate, the process can be reversed by use of pressure retarded osmosis (PRO). In this process, the salt gradient between the salt solution side (61) and the desalted water side (62) generates a hydraulic pressure over the osmosis membrane. Since the salt cannot pass through the membrane but the water, the water will pass the membrane towards the higher salinity (higher salt concentration) and thereby create hydraulic pressure, which then can be turned into electrical power through the generator (31). Depending on the salinity of the depressurized diluted salt solution, the stream can either go back (via 66) to the salt solution tank (64) or be let out of the system. An inlet (67) can supply the system with a fresh supply of salt solution.

Example 9. A Water Extraction System for Re-Extraction of Hemodialysis Water from Used Dialysis Solution This example shows the use of the water extraction system of the invention for post treatment of dialysate solution, cf. FIG. 1. The dialysate solution is a diluted aqueous solution of mineral ions and glucose, which typically runs in a counter-current flow with blood from a patient through a hollow fiber ultrafiltration module during hemodialysis. Sam et al. (2006) discloses composition and clinical use of hemodialysates. The dialysate solution will maintain a sufficient concentration gradient across an ultrafiltration membrane with respect to the solutes that have to be removed from the blood, such as urea, degradation products such as indoxyl sulphate and p-cresol, and excess potassium and phosphorous, and thus maintain efficiency of the dialysis. For this purpose large quantities of ultrapure water is needed, i.a. about 400 L of water per week. The water extraction systems described herein are useful in systems for reuse of this ultrapure water, such as in a closed loop where the (diluted) used dialysate solution, after being used in hemodialysis, e.g. after absorbing waste materials such as urea from blood by passing through a hemodialysis filter may function as the source solution (7) when passing through a further membrane module, i.e. the flow cell (1) containing an aquaporin membrane, and where a concentrated fresh dialysate solution (dialysis fluid) may function as the draw solution. Ideally, the concentrated dialysate can be sufficiently diluted so as to be directly used for continued hemodialysis. This could be achieved by applying a slight pressure on the feed side of the aquaporin containing membrane (using the concept of assisted forward osmosis). In this way only pure water is extracted from the contaminated, used dialysate solution and this extracted pure water is used as a replacement for the otherwise required new supplements of ultrapure water for dilution of the dialysate concentrate.

An additional advantage would result from the used dialysate solution becoming concentrated resulting in a smaller volume for waste disposal.

REFERENCES

Zhao, Y et al, Synthesis of robust and high-performance aquaporin-based biomimetic membranes by interfacial polymerization-membrane preparation and RO performance characterization, Journal of Membrane Science, Volumes 423-424, 15 Dec. 2012, Pages 422-428.

Kim et al. Journal of Membrane Science 419-420 (2012) 42-48.

Branislav Petrusevski, Saroj Sharma, Jan C. Schippers (UNESCO-IHE), and Kathleen Shordt (IRC), Reviewed by: Christine van Wijk (IRC). Arsenic in Drinking Water March 2007, IRC International Water and Sanitation Centre Nagaishi & Ishikawa (Geochemical Journal, Vol. 43, pp. 133 to 141, 2009)

Grosser, Z., Oct. 13, 2010 (downloaded from internet on 20130219): <url: http://www.watertechonline.com/articles/the-challenge-measure-arsenic-in-drinking-water>

Hill & Taylor, 15 Jul.-19 Jul. 2012, Use of Aquaporins to Achieve Needed Water Purity on the International Space Station for the Extravehicular Mobility Unit Space Suit System. In: (ICES) 42$^{nd}$ International Conference on Environmental systems, San Diego, Calif.

Al-Amoudi et al, Journal of Membrane Science 303 (2007) 4-28.

Porcelli et al, Separation and Purification Technology 71 (2010) 137-143

Achilli et al. Selection of inorganic-based draw solutions for forward osmosis applications. Journal of Membrane Science 364 (2010) 233-241

Phuntsho et al. A novel low energy fertilizer driven forward osmosis desalination for direct fertigation: Evaluating the performance of fertilizer draw solutions. Journal of Membrane Science 375 (2011) 172-181.

Sam et al. Composition and clinical use of hemodialysates. Hemodialysis International 2006; 10: 15-28

The invention claimed is:

1. A water extraction system for use in a fertigation system comprising:
   a) a flow cell comprising a membrane, said membrane comprising (i) an active layer comprising a cross linked aromatic polyamide thin film with immobilized aquaporin water channels and (ii) a support layer, and said membrane having a feed side and a non-feed side, wherein the non-feed side of the membrane functions as a draw side;
   b) an aqueous source solution in fluid communication with the feed side of the membrane;
   c) an aqueous draw solution in fluid communication with the draw side of the membrane, wherein the aqueous draw solution is a concentrated plant nutrient draw solution.

2. The water extraction system according to claim 1, wherein aquaporin vesicles are incorporated in the cross linked aromatic polyamide thin film, said vesicles being formed by self assembly of amphiphilic lipids or block copolymers in the presence of an aquaporin protein suspension.

3. The water extraction system according to claim 2 wherein said vesicles are formed from an amphiphilic lipid or triblock copolymer solution.

4. The water extraction system according to claim 1 wherein the aquaporin water channels are selected from a plant aquaporin, a mammal aquaporin, or a bacterial aquaporin.

5. The water extraction system according to claim 1 wherein said support layer is a polysulfone or polyether sulfone support membrane.

6. The water extraction system according to claim 1 further comprising means for regeneration or anti-fouling of said membrane, said means comprising a cleaning fluid having a pH of about 2 to 11, said cleaning fluid being selected from a solution of an organic acid or a chelating agent.

7. A fertigation system to produce a final product diluted plant nutrient solution, comprising:
   i) a feed stream being an aqueous source solution,
   ii) a pump receiving the feed stream,
   iii) a flow cell including a membrane, the membrane having a feed side and a non-feed side, wherein the non-feed side of the membrane functions as a draw side and the feed side is in fluid communication with the pump and the feed stream, the membrane including:
      a) an active layer having a cross linked aromatic polyamide thin film with immobilized aquaporin water channels, and
      b) a support layer,
   iv) an aqueous draw solution that flows into, and is in fluid communication with the draw side of the membrane, wherein the aqueous draw solution is a concentrated plant nutrient draw solution,
   v) a diluted draw solution that flows out from the draw side of the membrane, wherein the diluted draw solution is a diluted plant nutriment draw solution in comparison to the concentrated plant nutrient draw solution,
   (vi) an additionally diluted plant nutriment draw solution formed from at least one of:
      1) at least a portion of the diluted plant nutriment draw solution being re-circulated back into the concentrated plant nutrient draw solution to additionally dilute the concentrated plant nutrient draw solution, or
      2) freshwater in fluid communication with the diluted plant nutriment draw solution to additionally dilute the diluted plant nutriment draw solution, and
   vii) the final product diluted plant nutrient solution which is output from the fertigation system, the final product diluted plant nutrient solution being one of the diluted plant nutriment draw solution or the additionally diluted plant nutriment draw solution.

* * * * *